(12) United States Patent
Panayi et al.

(10) Patent No.: US 8,076,293 B2
(45) Date of Patent: Dec. 13, 2011

(54) USE OF BIP OR A VARIANT, HOMOLOGUE, DERIVATIVE OR FRAGMENT THEREOF IN THE MANUFACTURE OF A MEDICAMENT FOR THE PREVENTION OR TREATMENT OF BONE LOSS OR BONE RESORPTION

(76) Inventors: Gabriel Stavros Panayi, London (GB); Valerie Mary Corrigall, Tadworth (GB)

( * ) Notice: Subject to any disclaimer, the term of this patent is extended or adjusted under 35 U.S.C. 154(b) by 99 days.

(21) Appl. No.: 11/911,056

(22) PCT Filed: Apr. 18, 2006

(86) PCT No.: PCT/GB2006/001388
§ 371 (c)(1),
(2), (4) Date: Dec. 3, 2008

(87) PCT Pub. No.: WO2006/111720
PCT Pub. Date: Oct. 26, 2006

(65) Prior Publication Data
US 2009/0281026 A1 Nov. 12, 2009

(30) Foreign Application Priority Data

Apr. 19, 2005 (GB) .................................. 0507874.6
Apr. 20, 2005 (GB) .................................. 0507986.8

(51) Int. Cl.
*A61K 38/16* (2006.01)
*A61K 38/17* (2006.01)
(52) U.S. Cl. ..................... 514/16.7; 514/16.9; 514/16.8; 514/17.1; 514/21.2
(58) Field of Classification Search ........................ None
See application file for complete search history.

(56) References Cited

U.S. PATENT DOCUMENTS

| 4,946,779 A | 8/1990 | Kameda et al. | |
|---|---|---|---|
| 2003/0153048 A1* | 8/2003 | Goto et al. ................... | 435/69.2 |

FOREIGN PATENT DOCUMENTS

| EP | 0239400 A2 | 9/1987 |
|---|---|---|
| WO | 84/03564 A1 | 9/1984 |
| WO | 91/11172 A1 | 8/1991 |
| WO | 94/01557 A1 | 1/1994 |
| WO | 9402518 A1 | 2/1994 |
| WO | 98/55148 A1 | 12/1995 |
| WO | 00/21995 A1 | 4/2000 |
| WO | 02/72133 A1 | 9/2002 |

OTHER PUBLICATIONS

Wells, 1990, Biochemistry 29:8509-8517.*
Ngo et al., 1994, The Protein Folding Problem and Tertiary Structure Prediction, Merz et al., eds., Birkhauser, Boston, pp. 492-495.*
Bennett et al., J. Mol. Recognit., 8(1-2):52-58 (1995).
Bensadoun et al., Exp. Neurol., 164(1):15-24 (2000).
Berge et al., J. Pharm. Sci., 66(1):1-19 (1977).
Boyle et al., Nature, 423(6937):337-342 (2003).
Chambers, J. Pathol., 192(1):4-13 (2000).
Co et al., J. Immunol., 148(4):1149-1154 (1992).
Corrigall et al., Arthritis Rheum., 43(7):1606-1615 (2000).
Corrigall et al., Arthritis Rheum., 50(4):1164-1171 (2004).
Eferl et al., Nat. Rev. Cancer, 3(11):859-868 (2003).
Grigoriadis et al., Science, 266(5184):443-448 (1994).
Hong et al., J. Bone Miner. Res., 15(5):911-918 (2000).
Horwell, Trends Biotechnol., 13(4):132-134 (1995).
Huse et al., Science, 246(4935):1275-1281 (1989).
Jimi et al., Nat. Med., 10(6):617-624 (2004).
Koehler et al., Nature, 256(5517):495-497 (1975).
Kordower et al., Exp. Neurol., 160(1):1-16 (1999).
Lee et al., Biochem. Biophys. Res. Commun., 305(2):211-214 (2003).
Li et al., Gene Ther., 7(1):31-34 (2000).
Libouban et al., Bone, 33(3):283-292 (2003).
Maddox et al., J. Exp. Med., 158:1211 (1983).
Miossec et al., Arthritis Rheum., 37(12):1715-1722 (1994).
Nair et al., Calcif. Tissue Int., 64(3):214-218 (1999).
Neuberger et al., Nature, 312(5995):604-608 (1984).
Parce et al., Science, 246(4927):243-247 (1989).
Riechmann et al., Nature, 332(6162):323-327 (1988).
Rifas et al., J. Cell Biochem., 88(4):650-659 (2003).
Roberge et al., Science, 269(5221):202-204 (1995).
Roodman, Exp. Hematol., 27(8):1229-1241 (1999).
Senter et al., Adv. Drug Deliv. Rev., 53(3):247-264 (2001).
Sodek et al., Connect. Tissue Res., 43(2-3):308-319 (2002).
Takayanagi et al., Arthritis Rheum, 43(2):259-269 (2000).
Takayanagi et al., Dev. Cell, 3(6):889-901 (2002).
Takeda et al., Nature, 314(6010):452-454 (1985).
Tatusova et al., FEMS Microbiol. Lett., 174(2):247-250 (1999).
Teti et al., Calcif. Tissue Int., 71(4):293-299 (2002).
Udagawa, J. Bone Miner Metab., 21(6):337-343 (2003).
Verhoeyen et al., Science, 239(4847):1534-1536 (1988).
Vignery, Int. J. Exp. Pathol., 81(5):291-304 (2000).
Vile et al., Ann. Oncol., 5 Suppl 4:59-65 (1994).
Wagner et al., Curr. Opin. Genet. Dev., 11(5):527-532 (2001).
Walsh et al., Curr. Opin. Rheumatol., 16(4):419-427 (2004).
Winter et al., Nature, 349(6307):293-299 (1991).
Yang et al., Gene Ther., 11(5):483-491 (2004).
Alemany, Cancer Gene Ther., 6:21-25 (1999).
Zwerina et al., Arthritis Rheum., 50(1):277-290 (2004).
Tatusova et al., FEMS Microbiol. Lett., 177(1):187-188 (1999).
Morrison et al., Proc. Natl. Acad. Sci. USA, 81(21):6851-6855 (1984).
Orlandi et al., Proc. Natl. Acad. Sci. USA, 86(10):3833-3837 (1989).
Owicki et al., Proc. Natl. Acad. Sci. USA, 87(10):4007-4011 (1990).
Ralston, BMJ, 315(7106):469-472 (1997).
Sato et al., Cancer Res., 53(4):851-856 (1993).
Simon et al., Proc. Natl. Acad. Sci. USA, 89(20):9367-9371 (1992).
Suda et al., Endocr. Rev., 20(3):345-357 (1999).
Sunters et al., J. Biol. Chem., 279(11):9882-9891 (2004).

(Continued)

*Primary Examiner* — Elizabeth C Kemmerer
(74) *Attorney, Agent, or Firm* — McAndrews Held & Malloy Ltd.

(57) ABSTRACT

The present invention relates to the use of BiP or a variant, homologue, derivative or fragment thereof in the manufacture of a medicament for the prevention or treatment of bone loss or bone resorption.

9 Claims, 6 Drawing Sheets

OTHER PUBLICATIONS

Vittecoq et al., Rheumatology (Oxford), 42(8):939-946 (2003).
Bodman-Smith et al., Rheumatology (Oxford), 42(5):637-644 (2003).
Boussif et al., Proc. Natl. Acad. Sci. USA, 92(16):7297-7301 (1995).
Corrigall et al., J. Immunol., 166(3):1492-1498 (2001).
Corrigall et al., J. Immunol., 166(6):4141-4147 (2001).
Cote et al., Proc. Natl. Acad. Sci. USA, 80(7):2026-2030 (1983).
Degli-Esposti, J. Leukoc. Biol., 65(5):535-542 (1999).
Devereux et al., Nucleic Acids Res., 12(1 Pt 1):387-395 (1984).
Fynan et al., Proc. Natl. Acad. Sci. USA., 90(24):11478-11482 (1993).
Gorman et al., Proc. Natl. Acad. Sci. USA, 88(10):4181-4185 (1991).
Johanson et al., J. Biol. Chem., 270(16):9459-9471 (1995).
Lubberts et al., J. Immunol., 170(5):2655-2662 (2003).

* cited by examiner

USE OF BIP OR A VARIANT, HOMOLOGUE, DERIVATIVE OR FRAGMENT THEREOF IN THE MANUFACTURE OF A MEDICAMENT FOR THE PREVENTION OR TREATMENT OF BONE LOSS OR BONE RESORPTION

The present application is filed Pursuant to 35 U.S.C. 371 as a U.S. National Phase application of International Patent Application No. PCT/GB2006/001388, which was filed Apr. 18, 2006, claiming the benefit of priority of Great Britain Patent Application No. 0507874.6, which was filed on Apr. 19, 2005, and of Great Britain Patent Application No. 0507986.8, which was filed on Apr. 20, 2005.

FIELD OF INVENTION

The present invention relates to the use of BiP in the manufacture of a composition for the prevention or treatment of bone loss or bone resorption. The present invention also relates to methods—such as diagnostic methods and assay methods—pharmaceutical compositions, transgenic animals and methods for preparing same.

BACKGROUND TO THE INVENTION

Dysregulated bone remodelling is a major part of the pathology of a number of diseases. In such conditions accelerated production and activation of the bone resorbing osteoclast population results from an as yet unidentified aberrant network of mediators. In the past ten years, the major signalling pathways and transcription factors controlling the commitment and differentiation of haematopoietic stem cells and monocyte/macrophage precursors to the osteoclast lineage, osteoclast proliferation and activation have been identified (1-5). It is now recognised that signalling via the constitutively expressed Receptor Activator of NF-κB (RANK) on osteoclast precursors following binding to RANK ligand (RANKL), in conjunction with activation by macrophage-colony stimulating factor (M-CSF), results in a complex series of events leading to the production of mature osteoclasts. In vivo both M-CSF and RANKL are provided by osteoblasts, which, together with the decoy receptor osteoprotegerin (OPG) (6-7), serve to regulate osteoclast differentiation and bone resorption. It is via the osteoblast component that systemic hormones and cytokines act indirectly to influence this process, with the relative ratio of RANKL to OPG critically controlling osteoclastogenesis. In pathological states (such as rheumatoid arthritis (RA)) however, RANKL can be provided additionally by activated T cells, fibroblast-like synoviocytes and other stromal cells (8-10). RANKL-RANK binding activates cell signalling cascades through several key stages. The process relies on the recruitment of TNF receptor-associated factor proteins (TRAFs), mitogen-activated protein kinase cascades (ERK, JNK and p38) in addition to Src- and phosphatidylinositol-3-kinase (PI3K) mediated activation of Akt, and all these RANK signalling pathways ultimately converge to activate several transcription factor families—such as NF-κB (11), activator protein-1 (AP-1) (12), particularly c-Fos (13), and Nuclear Factor of Activated T cells (NFAT), specifically NFATc1 (1;5; 14;15). That these signalling molecules and transcription factors have essential roles in osteoclast differentiation and activation has been demonstrated unequivocally in loss-of-function mouse mutants in vivo (5).

The anti-inflammatory properties of a human molecular chaperone known variously as binding immunoglobulin protein (BiP) or glucose regulated protein (Grp)78 have been reported (17). The gene encoding BiP has been cloned and the recombinant human (rhu) protein expressed (WO 00/21995).

Administration of rhuBiP to mice with collagen-induced arthritis (CIA), prevented the induction of experimental arthritis (17). An indication of the anti-inflammatory mechanism of action of BiP, was the finding that T cell clones responsive to rhuBiP produced the cytokines, IL-10, IL-4 and IL-5 (18) and that BiP-stimulated peripheral blood (PB) mononuclear cells (MC) produced high concentrations of IL-10 with concomitant attenuation of TNF-α production. PBMC also produced increased amounts of IL-1R antagonist and soluble TNFRII (19). Cytokines released from PBMC in response to BiP regulate osteoclastogenesis (20;21).

To reinforce the fact that these extracellular functions of BiP have biological relevance, immunoassay of synovial fluids has revealed that the majority of those from patients with RA contain soluble BiP (19). It is also known that the antigen presenting function of monocytes (MO) is reduced following downregulation of CD86 and HLA-DR expression (19) and that BiP delays and prevents the maturation of purified PBMO into immature dendritic cells (iDC) (22).

The use of BiP in the manufacture of a medicament for the treatment of an unwanted immune response is described in WO02/072133.

Bone is continually made or digested by specialist cells called osteoblasts and osteoclasts respectively. There are many diseases in which bone erosion or thinning occurs due to an imbalance between bone formation and bone dissolution. Accordingly, there is a need in the art to develop drugs that modulate (e.g. prevent) this process.

SUMMARY OF THE INVENTION

The present invention is based, in part, on the surprising finding that BiP inhibits, prevents or diminishes bone resorption and maturation of osteoclasts. Without wishing to be bound by any particular theory, this inhibition is believed to be effective through the modulation of essential signalling pathways, which are activated during the process of differentiation. Accordingly, BiP has therapeutic application in modulating inter alia bone loss.

In WO02/072133, it is taught that BiP has immunomodulatory properties and the use of BiP in treating or preventing an unwanted immune response is described. Furthermore, the use of BiP in treating auto-immune diseases is disclosed. By way of example, this citation teaches that human blood mononuclear cells cultured with BiP release IL-10 which may downregulate auto-immune diseases discussed therein—such as rheumatoid arthritis (RA). Moreover, Corrigall et al. (17) teach that BiP can be used to inhibit the development of rheumatoid arthritis and is a candidate for the immunotherapy of this disorder. Thus, whilst the immunomodulatory and anti-inflammatory properties of BiP have been described, there is no disclosure in the prior art of the surprising finding presented herein that BiP can directly modulate bone resorption and maturation of osteoclasts.

In vitro osteoclast differentiation assays, using both mouse bone marrow macrophages (BMM) and human PBMC cultured in the presence of M-CSF and RANKL were used. The results show that in both mouse and human differentiation assays the number of osteoclasts visualised by either staining for tartrate-resistant acid phosphatase (TRAP), vitronectin receptor (VnR, αvβ3) or the presence of F-actin rings was reduced and this was paralleled by decreases in resorptive activity (FIG. 3). Moreover, addition of BiP to mature osteoclasts reduced the osteoclast number (FIG. 4). Also in a further series of experiments that are described herein, global changes in gene expression in purified PBMO in response to BiP has been investigated. Experiments using Affymetrix gene array technology have shown that BiP treatment of purified PBMO causes down-regulation as well as up-regulation of many genes, when compared with unstimulated PBMO. BiP downregulates the expression of VnR (24), CD44 (25), osteopontin (26), IKK (14) and c-Fos (13), all of which have important roles in, or are essential for osteoclast differentiation (FIG. 5).

SUMMARY ASPECTS OF THE PRESENT INVENTION

In a first aspect, there is provided the use of BiP or a variant, homologue, derivative or fragment thereof in the manufacture of a medicament for the prevention or treatment of bone loss.

In a second aspect, there is provided the use of BiP or a variant, homologue, derivative or fragment thereof in the manufacture of a medicament for the prevention or treatment of bone resorption.

In a third aspect, there is provided the use of BiP in the modulation of osteoclast maturation.

In a fourth aspect, there is provided a method for preventing or treating bone loss comprising administering BiP or a variant, homologue, derivative or fragment thereof to cause a beneficial preventative or therapeutic effect.

In a fifth aspect, there is provided a method for preventing or treating bone resorption comprising administering BiP or a variant, homologue, derivative or fragment thereof to cause a beneficial preventative or therapeutic effect.

In a sixth aspect, there is provided a method for modulating osteoclast development comprising contacting an osteoclast with BiP or a variant, homologue, derivative or fragment thereof.

In a seventh aspect, there is provided a method of diagnosis of a disease or syndrome caused by or associated with bone loss comprising the steps of: (a) detecting BiP activity in a subject; (b) comparing the BiP activity with that of an unaffected control; and (c) comparing the value obtained from the control with the value obtained from the subject; wherein a difference between the value obtained from the control and the value obtained from the subject is indicative that the subject is suffering from the disease or syndrome.

In an eighth aspect, there is provided an assay method for identifying an agent that modulates bone destruction or bone loss comprising the steps of: (i) selecting an agent which modulates BiP activity; and (ii) measuring osteoclast maturation in the presence of said agent; wherein a difference between osteoclast maturation in the absence of the agent and osteoclast maturation in the presence of the agent is indicative of an agent that modulates bone destruction or bone loss.

In a ninth aspect, there is provided a process comprising the steps of: (a) performing the assay method according to the eighth aspect of the present invention; (b) identifying one or more agents that do modulate bone destruction or bone loss; and (c) preparing a quantity of those one or more identified agents.

In a tenth aspect, there is provided an agent obtained by the assay method according to the eighth aspect of the present invention.

In a eleventh aspect, there is provided a method for determining the effect(s) of BiP or a variant, homologue, derivative or fragment thereof on osteoclast differentiation comprising the steps of: (a) adding BiP to one or more osteoclasts which are at one or more different stages of osteoclast differentiation; and (b) determining the effect(s) of BiP on osteoclastogenesis.

In a twelfth aspect, the present invention relates to a method for identifying one or more proteins that are modulated by BiP during osteoclast differentiation, comprising the steps of: (a) differentiating an osteoclast in the presence and in the absence of BiP; and (b) identifying one or more proteins that are differentially expressed in an osteoclast differentiated in the presence of BiP compared to an osteoclast differentiated in the absence of BiP.

In a thirteenth aspect, the present invention relates to the use of BiP or a variant, homologue, derivative or fragment thereof in the manufacture of a medicament for the prevention or treatment of osteoporosis.

PREFERRED EMBODIMENTS

Preferably the invention relates to use of BiP for the manufacture of a medicament for bone loss.

Preferably the invention relates to use of BiP for the manufacture of a medicament for bone resorption.

Preferably the invention relates to BiP for use in the treatment of bone loss.

Preferably the invention relates to BiP for use in the treatment of bone resorption.

Preferably the bone loss or bone resorption is bone destruction associated with cancer or cancer metastasis. This bone destruction has the same biological basis as the other forms of bone loss discussed herein.

Preferably, the bone loss or bone resorption is associated with musculoskeletal disease. Preferably, the musculoskeletal disease is osteoporosis.

Preferably, the modulation is inhibition, reduction or prevention of osteoclast maturation or development.

Preferably, the modulation of osteoclast maturation is performed in vivo or in vitro.

Preferably, the osteoclast is an osteoclast precursor, a multi-nucleated precursor or a mature osteoclast.

Preferably, in the method according to the seventh aspect of the present invention, BiP activity is decreased in comparison to the values obtained from a control.

Preferably, the method according to the seventh aspect of the present invention comprises the optional step of measuring osteoclast development or bone resorption Preferably, the agent(s) described herein increases or upregulates BiP activity.

Preferably, in the method according to the eleventh aspect of the present invention, BiP is added at a concentration of from 0.02-20 µg/ml.

Preferably, the number of osteoclasts is quantified by measuring TRAP activity, VnR and/or F-actin rings.

Preferably, the method according to the eleventh aspect of the present invention comprises the optional step of quantifying bone resorption.

Preferably, osteoclast differentiation is confirmed using PCR to measure the expression of one or more osteoclast specific markers.

Preferably, the osteoclast specific marker(s) is the calcitonin receptor gene or cathepsin K gene.

Preferably, the protein(s) identified in accordance with the twelfth aspect of the present invention is a signalling molecule or a transcription factor.

Preferably, BiP is added for a 24-72 hr period either at the beginning of the culture or towards the end of the culture when multinucleated osteoclasts are present in the method according to the twelfth aspect of the present invention.

Preferably, the nucleic acid encoding the protein(s) or the protein(s) is detected using qt-RT-PCR and/or Western blotting.

Figure 1:
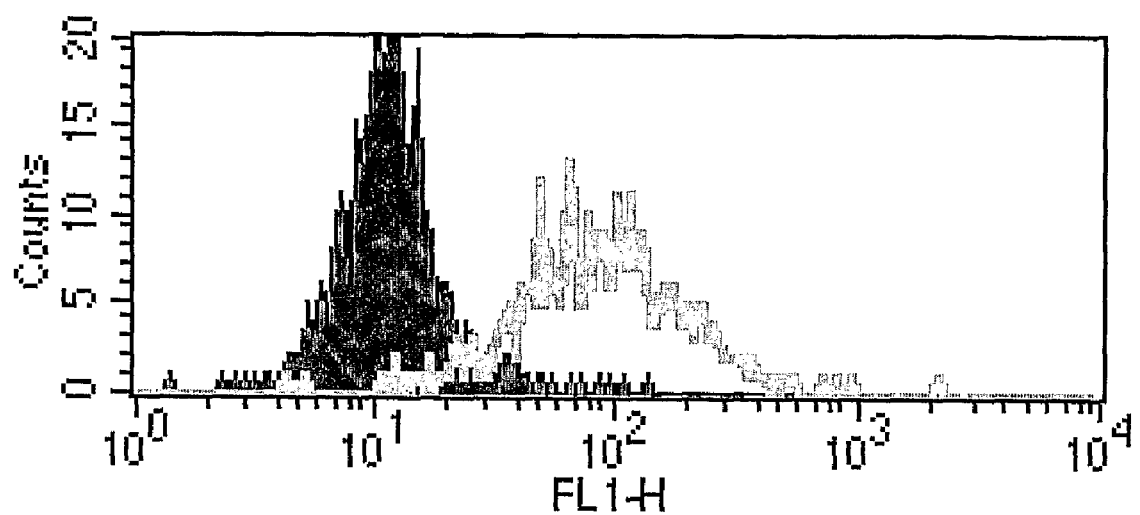
FIG. 1
Figure 2:
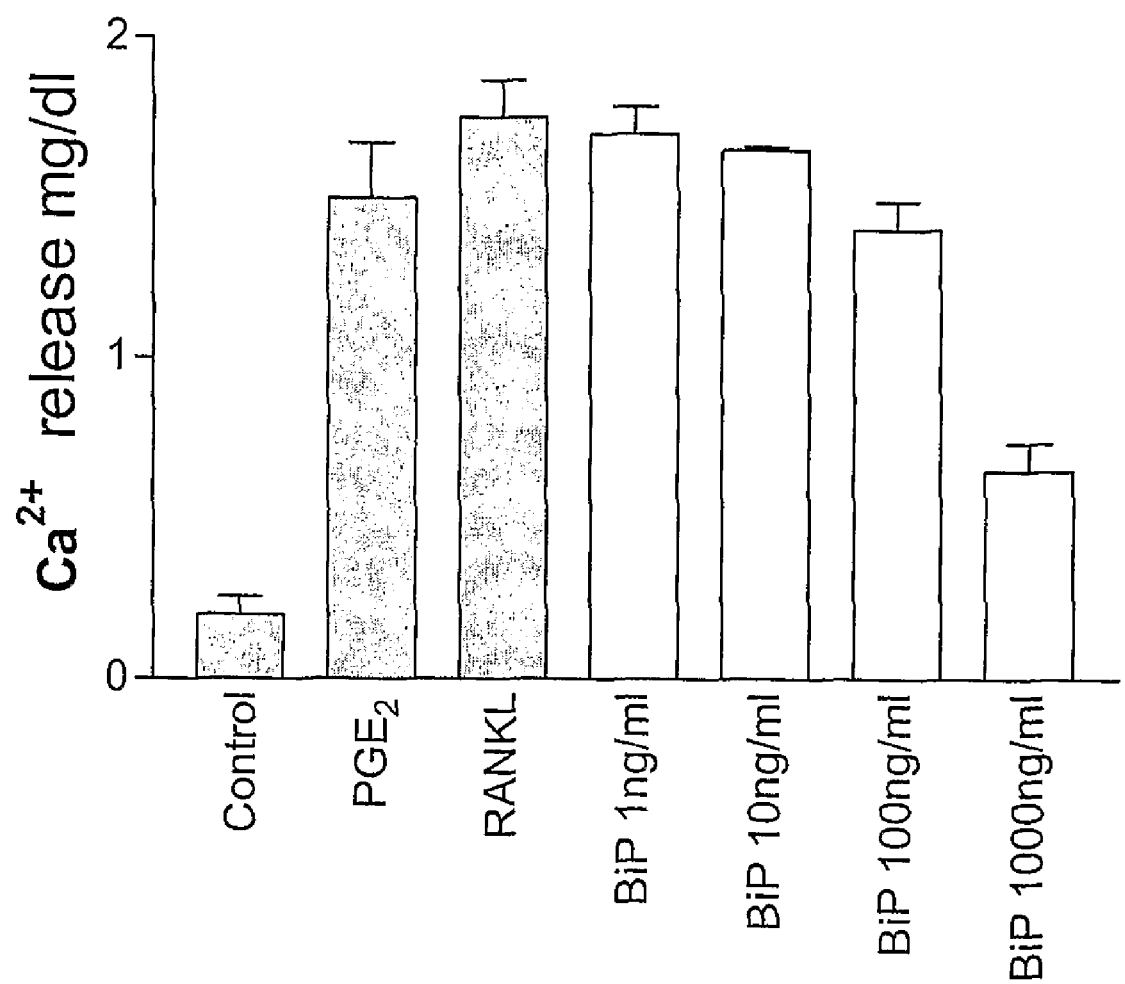
Figure 3:
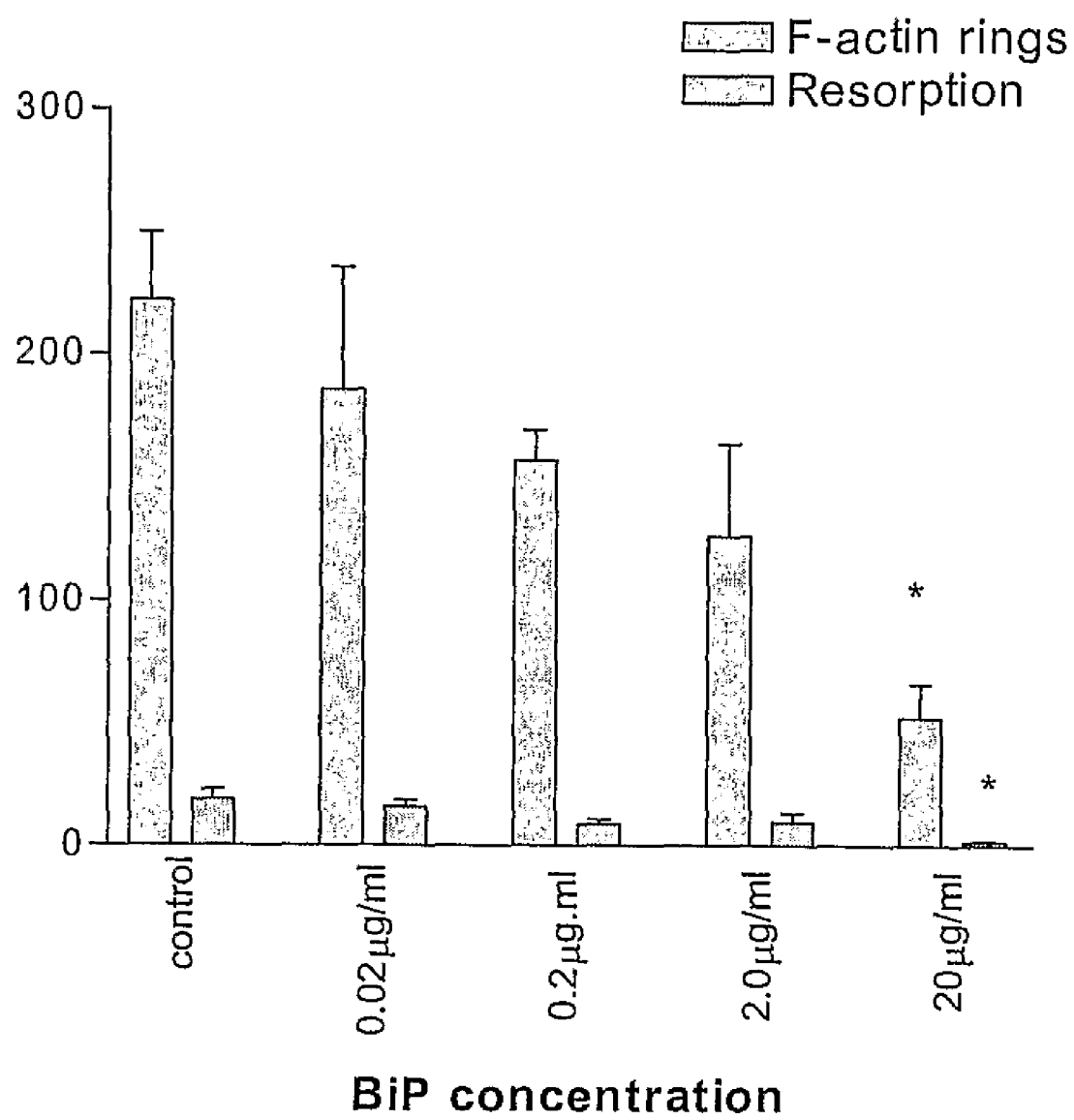
Figure 4:
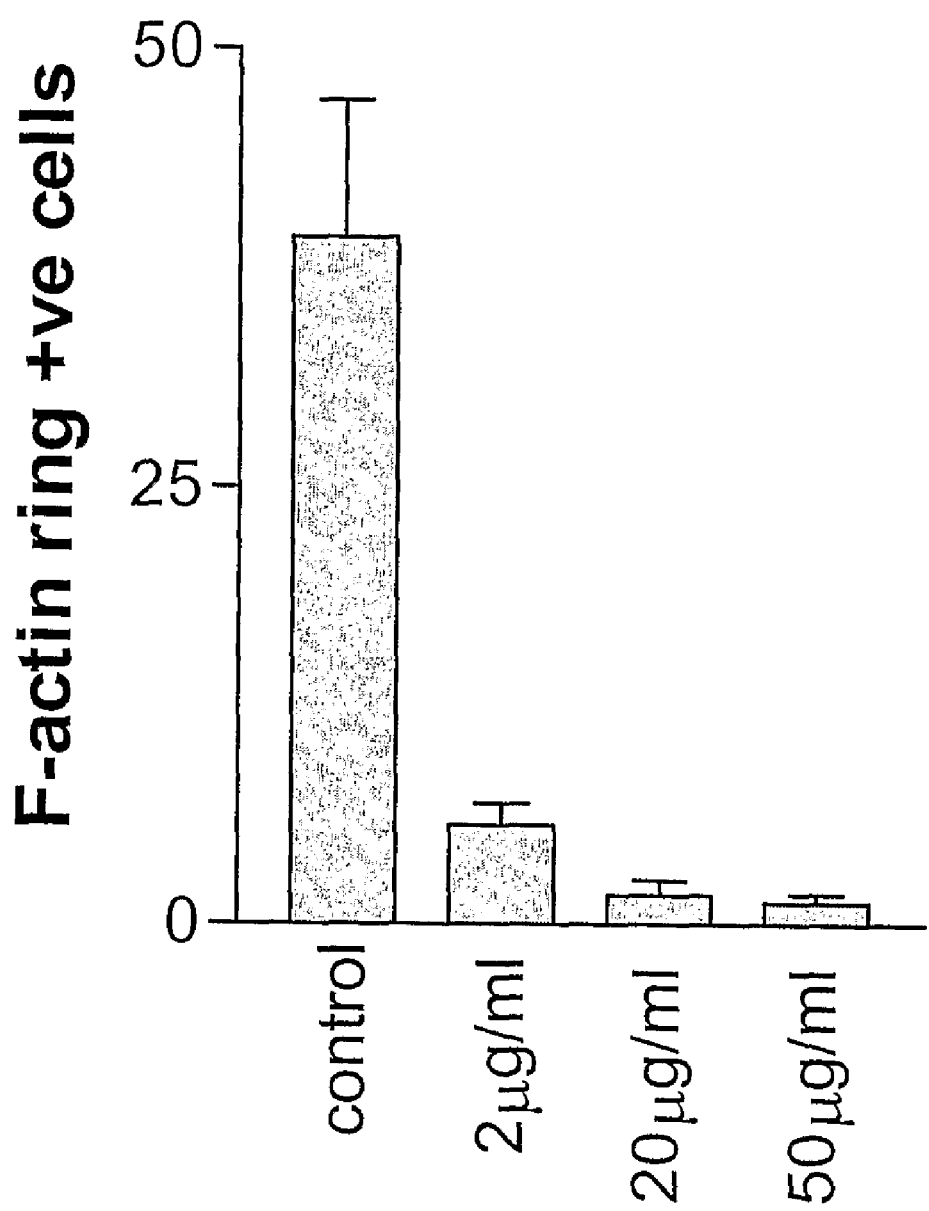
Figure 5:
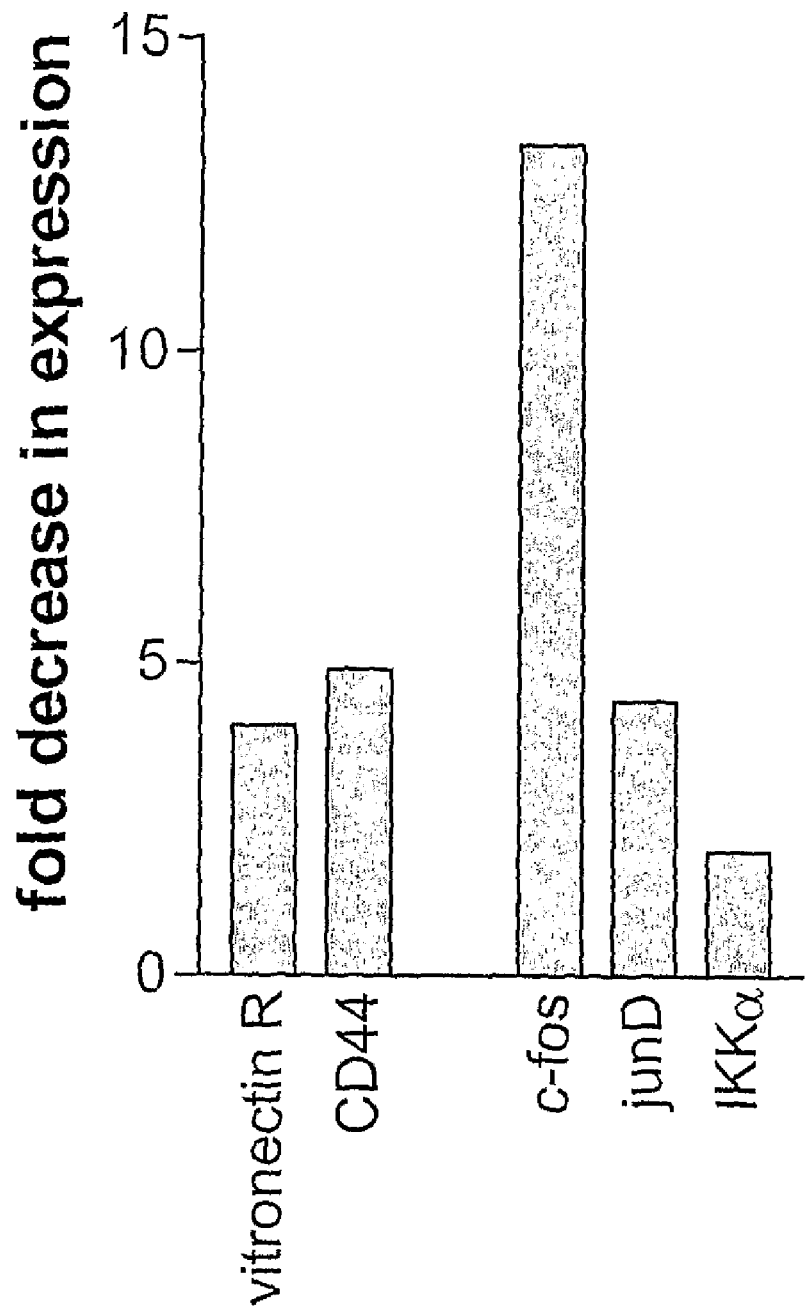

BiP.FITC binding to peripheral blood monocytes. Human serum albumin.FITC (solid) or BiP.FITC (open) were used to stain human monocytes for 20 mins at 4° C. and the fluorescence measured by flow cytometry. The FACscan histogram was generated using Cellquest software.

FIG. 2

BiP inhibits bone resorption in the murine calvarial model. BiP (1-1000 ng/ml) was added to mouse calvariae incubated with RANKL for 5 days. Bone resorption was determined by calcium release.

FIG. 3

The effect of BiP on osteoclast differentiation when added with M-CSF and RANKL. TRITC-phalloidin was used to detect F-actin ring positive cells following 14 days culture of human monocytes with BiP (0.02-20 μg/ml) and M-CSF+RANKL compared with control cultures with M-CSF+RANKL alone. Bone resorption was measured by toluidine blue staining of resorption lacunae on dentine slices. *p<0.03.

FIG. 4

Addition of BiP to mature osteoclasts. BiP (2-50 μg/ml) was added to mature human osteoclasts at day 10. At day 14 cells positive for F-actin rings were measured using TRITC-phalloidin.

FIG. 5

The fold decrease of gene activity, induced by BiP, measured by Affymetrix gene array. Duplicate Affymetrix gene array chips were analysed using purified human monocytes prepared by negative immunomagnetic selection and cultured either in the absence or presence of BiP (20 μg/ml) for 24 hours. The fold difference in expression was calculated by the difference in gene expression between the BiP treated and resting cells. All data were analysed by GeneSpring software.

FIG. 6

Affymetrix gene array analysis. Purified monocytes were either stimulated with BiP or unstimulated and the gene activation measured and compared in duplicate samples. Those genes that were also recorded as being similarly up- or down-regulated in the R&D cytokine gene array (*) or that have been verified by flow cytometry and/or protein production (_) are marked as such. A fold decrease of −20 is a schematic indication of the absence of gene activity in the BiP treated monocytes.

DETAILED DESCRIPTION OF THE INVENTION

BiP

As used herein, the term "BiP" refers to the 78 kD endoplasmic reticulum chaperone protein as disclosed in WO 00/21995. Preferably the BiP polypeptide has the amino acid sequence as shown in appendix 2 of WO00/21995 at page 23.

```
Met Glu Glu Asp Lys Lys Glu Asp Val Gly Thr Val Val Gly Ile Asp   (SEQ ID NO. 1)
 1               5                  10                  15

Leu Gly Thr Thr Tyr Ser Cys Val Gly Val Phe Lys Asn Gly Arg Val
                 20                  25                  30

Glu Ile Ile Ala Asn Asp Gln Gly Asn Arg Ile Thr Pro Ser Tyr Val
             35                  40                  45

Ala Phe Thr Pro Glu Gly Glu Arg Leu Ile Gly Asp Ala Ala Lys Asn
         50                  55                  60

Gln Leu Thr Ser Asn Pro Glu Asn Thr Val Phe Asp Ala Lys Arg Leu
 65                  70                  75                  80

Ile Gly Arg Thr Trp Asn Asp Pro Ser Val Gln Gln Asp Ile Lys Phe
                 85                  90                  95

Leu Pro Phe Lys Val Val Glu Lys Lys Thr Lys Pro Tyr Ile Gln Val
                100                 105                 110

Asp Ile Gly Gly Gly Gln Thr Lys Thr Phe Ala Pro Glu Glu Ile Ser
            115                 120                 125

Ala Met Val Leu Thr Lys Met Lys Glu Thr Ala Glu Ala Tyr Leu Gly
        130                 135                 140

Lys Lys Val Thr His Ala Val Val Thr Val Pro Ala Tyr Phe Asn Asp
145                 150                 155                 160

Ala Gln Arg Gln Ala Thr Lys Asp Ala Gly Thr Ile Ala Gly Leu Asn
                165                 170                 175

Val Met Arg Ile Ile Asn Glu Pro Thr Ala Ala Ala Ile Ala Tyr Gly
            180                 185                 190

Leu Asp Lys Arg Glu Gly Glu Lys Asn Ile Leu Val Phe Asp Leu Gly
        195                 200                 205

Gly Gly Thr Phe Asp Val Ser Leu Leu Thr Ile Asp Asn Gly Val Phe
    210                 215                 220

Glu Val Val Ala Thr Asn Gly Asp Thr His Leu Gly Gly Glu Asp Phe
225                 230                 235                 240
```

-continued

```
Asp Gln Arg Val Met Glu His Phe Ile Lys Leu Tyr Lys Lys Thr
            245                 250                 255

Gly Lys Asp Val Arg Lys Asp Asn Arg Ala Val Gln Lys Leu Arg Arg
            260                 265                 270

Glu Val Glu Lys Ala Lys Arg Ala Leu Ser Ser Gln His Gln Ala Arg
            275                 280                 285

Ile Glu Ile Glu Ser Phe Tyr Glu Gly Glu Asp Phe Ser Glu Thr Leu
            290                 295                 300

Thr Arg Ala Lys Phe Glu Glu Leu Asn Met Asp Leu Phe Arg Ser Thr
305                 310                 315                 320

Met Lys Pro Val Gln Lys Val Leu Glu Asp Ser Asp Leu Lys Lys Ser
            325                 330                 335

Asp Ile Asp Glu Ile Val Leu Val Gly Gly Ser Thr Arg Ile Pro Lys
            340                 345                 350

Ile Gln Gln Leu Val Lys Glu Phe Phe Asn Gly Lys Glu Pro Ser Arg
            355                 360                 365

Gly Ile Asn Pro Asp Glu Ala Val Ala Tyr Gly Ala Ala Val Gln Ala
            370                 375                 380

Gly Val Leu Ser Gly Asp Gln Asp Thr Gly Asp Leu Val Leu Leu Asp
385                 390                 395                 400

Val Cys Pro Leu Thr Leu Gly Ile Glu Thr Val Gly Gly Val Met Thr
            405                 410                 415

Lys Leu Ile Pro Arg Asn Thr Val Val Pro Thr Lys Lys Ser Gln Ile
            420                 425                 430

Phe Ser Thr Ala Ser Asp Asn Gln Pro Thr Val Thr Ile Lys Val Tyr
            435                 440                 445

Glu Gly Glu Arg Pro Leu Thr Lys Asp Asn His Leu Leu Gly Thr Phe
            450                 455                 460

Asp Leu Thr Gly Ile Pro Pro Ala Pro Arg Gly Val Pro Gln Ile Glu
465                 470                 475                 480

Val Thr Phe Glu Ile Asp Val Asn Gly Ile Leu Arg Val Thr Ala Glu
            485                 490                 495

Asp Lys Gly Thr Gly Asn Lys Asn Lys Ile Thr Ile Thr Asn Asp Gln
            500                 505                 510

Asn Arg Leu Thr Pro Glu Glu Ile Glu Arg Met Val Asn Asp Ala Glu
            515                 520                 525

Lys Phe Ala Glu Glu Asp Lys Lys Leu Lys Glu Arg Ile Asp Thr Arg
            530                 535                 540

Asn Glu Leu Glu Ser Tyr Ala Tyr Ser Leu Lys Asn Gln Ile Gly Asp
545                 550                 555                 560

Lys Glu Lys Leu Gly Gly Lys Leu Ser Ser Glu Asp Lys Glu Thr Met
            565                 570                 575

Glu Lys Ala Val Glu Glu Lys Ile Glu Trp Leu Glu Ser His Gln Asp
            580                 585                 590

Ala Asp Ile Glu Asp Phe Lys Ala Lys Lys Lys Glu Leu Glu Glu Ile
            595                 600                 605

Val Gln Pro Ile Ile Ser Lys Leu Tyr Gly Ser Ala Gly Pro Pro
            610                 615                 620

Thr Gly Glu Glu Asp Thr Ala Glu Leu His His His His His
625                 630                 635

Met Glu Glu Asp Lys Lys Glu Asp Val Gly Thr Val Val Gly Ile Asp    (SEQ ID NO. 2)
  1              5                  10                   15

Leu Gly Thr Thr Tyr Ser Cys Val Gly Val Phe Lys Asn Gly Arg Val
             20                   25                  30
```

```
Glu Ile Ile Ala Asn Asp Gln Gly Asn Arg Ile Thr Pro Ser Tyr Val
         35                  40                  45

Ala Phe Thr Pro Glu Gly Arg Leu Ile Gly Asp Ala Ala Lys Asn
 50                  55                  60

Gln Leu Thr Ser Asn Pro Glu Asn Thr Val Phe Asp Ala Lys Arg Leu
 65                  70                  75                  80

Ile Gly Arg Thr Trp Asn Asp Pro Ser Val Gln Gln Asp Ile Lys Phe
                 85                  90                  95

Leu Pro Phe Lys Val Val Glu Lys Lys Thr Lys Pro Tyr Ile Gln Val
            100                 105                 110

Asp Ile Gly Gly Gly Gln Thr Lys Thr Phe Ala Pro Glu Glu Ile Ser
        115                 120                 125

Ala Met Val Leu Thr Lys Met Lys Glu Thr Ala Glu Ala Tyr Leu Gly
    130                 135                 140

Lys Lys Val Thr His Ala Val Val Thr Val Pro Ala Tyr Phe Asn Asp
145                 150                 155                 160

Ala Gln Arg Gln Ala Thr Lys Asp Ala Gly Thr Ile Ala Gly Leu Asn
                165                 170                 175

Val Met Arg Ile Ile Asn Glu Pro Thr Ala Ala Ile Ala Tyr Gly
            180                 185                 190

Leu Asp Lys Arg Glu Gly Glu Lys Asn Ile Leu Val Phe Asp Leu Gly
        195                 200                 205

Gly Gly Thr Phe Asp Val Ser Leu Leu Thr Ile Asp Asn Gly Val Phe
    210                 215                 220

Glu Val Val Ala Thr Asn Gly Asp Thr His Leu Gly Gly Glu Asp Phe
225                 230                 235                 240

Asp Gln Arg Val Met Glu His Phe Ile Lys Leu Tyr Lys Lys Lys Thr
                245                 250                 255

Gly Lys Asp Val Arg Lys Asp Asn Arg Ala Val Gln Lys Leu Arg Arg
            260                 265                 270

Glu Val Glu Lys Ala Lys Arg Ala Leu Ser Ser Gln His Gln Ala Arg
        275                 280                 285

Ile Glu Ile Glu Ser Phe Tyr Glu Gly Glu Asp Phe Ser Glu Thr Leu
    290                 295                 300

Thr Arg Ala Lys Phe Glu Glu Leu Asn Met Asp Leu Phe Arg Ser Thr
305                 310                 315                 320

Met Lys Pro Val Gln Lys Val Leu Glu Asp Ser Asp Leu Lys Lys Ser
                325                 330                 335

Asp Ile Asp Glu Ile Val Leu Val Gly Gly Ser Thr Arg Ile Pro Lys
            340                 345                 350

Ile Gln Gln Leu Val Lys Glu Phe Phe Asn Gly Lys Glu Pro Ser Arg
        355                 360                 365

Gly Ile Asn Pro Asp Glu Ala Val Ala Tyr Gly Ala Ala Val Gln Ala
    370                 375                 380

Gly Val Leu Ser Gly Asp Gln Asp Thr Gly Asp Leu Val Leu Leu Asp
385                 390                 395                 400

Val Cys Pro Leu Thr Leu Gly Ile Glu Thr Val Gly Gly Val Met Thr
                405                 410                 415

Lys Leu Ile Pro Arg Asn Thr Val Val Pro Thr Lys Lys Ser Gln Ile
            420                 425                 430

Phe Ser Thr Ala Ser Asp Asn Gln Pro Thr Val Thr Ile Lys Val Tyr
        435                 440                 445

Glu Gly Glu Arg Pro Leu Thr Lys Asp Asn His Leu Leu Gly Thr Phe
    450                 455                 460
```

-continued

```
Asp Leu Thr Gly Ile Pro Pro Ala Pro Arg Gly Val Pro Gln Ile Glu
465                 470                 475                 480
Val Thr Phe Glu Ile Asp Val Asn Gly Ile Leu Arg Val Thr Ala Glu
                485                 490                 495
Asp Lys Gly Thr Gly Asn Lys Asn Lys Ile Thr Ile Thr Asn Asp Gln
            500                 505                 510
Asn Arg Leu Thr Pro Glu Glu Ile Glu Arg Met Val Asn Asp Ala Glu
        515                 520                 525
Lys Phe Ala Glu Glu Asp Lys Lys Leu Lys Glu Arg Ile Asp Thr Arg
    530                 535                 540
Asn Glu Leu Glu Ser Tyr Ala Tyr Ser Leu Lys Asn Gln Ile Gly Asp
545                 550                 555                 560
Lys Glu Lys Leu Gly Gly Lys Leu Ser Ser Glu Asp Lys Glu Thr Met
                565                 570                 575
Glu Lys Ala Val Glu Glu Lys Ile Glu Trp Leu Glu Ser His Gln Asp
            580                 585                 590
Ala Asp Ile Glu Asp Phe Lys Ala Lys Lys Lys Glu Leu Glu Glu Ile
        595                 600                 605
Val Gln Pro Ile Ile Ser Lys Leu Tyr Gly Ser Ala Gly Pro Pro Pro
    610                 615                 620
Thr Gly Glu Glu Asp Thr Ala Glu Leu
625                 630
```

```
atggaggagg acaagaagga ggacgtgggc acggtggtcg gcatcgacct ggggaccacc      60   (SEQ ID NO. 3)
tactcctgcg tcggcgtgtt caagaacggc cgcgtggaga tcatcgccaa cgatcagggc     120
aaccgcatca cgccgtccta tgtcgccttc actcctgaag ggaacgtctc gattggcgat     180
gccgccaaga accagctcac ctccaacccc gagaacacgg tctttgacgc aagcgggctc     240
atcggccgca cgtggaatga cccgtctgtg cagcaggaca tcaagttctt gccgttcaag     300
gtggttgaaa agaaaactaa accatacatt caagttgata ttggaggtgg caaacaaag     360
acatttgctc ctgaagaaat ttctgccatg gttctcacta aaatgaaaga aaccgctgag     420
gcttatttgg gaagaaggt tacccatgca gttgttactg taccagccta tttaatgat      480
gcccaacgcc aagcaaccaa agacgctgga actattgctg gcctaaatgt tatgaggatc     540
atcaacgagc ctacggcagc tgctattgct tatggcctgg ataagaggga gggggagaag     600
aacatcctgt gttttgacct gggtggcgga accttcgatg tgtctcttct caccattgac     660
aatggtgtct tcgaagttgt ggccactaat ggagatactc atctgggtgg agaagacttt     720
gaccagcgtg tcatggaaca cttcatcaaa ctgtacaaaa agaagacggg caaagatgtc     780
aggaaagaca atagagctgt gcagaaactc cggcgcgagg tagaaaaggc caaacgggcc     840
ctgtcttctc agcatcaagc aagaattgaa attgagtcct ctatgaagg agaagacttt     900
tctgagaccc tgactcgggc caaatttgaa gagctcaaca tggatctgtt ccggtctact     960
atgaagcccg tccagaaagt gttggaagat tctgatttga agaagtctga tattgatgaa    1020
attgttcttg ttggtggctc gactcgaatt ccaaagattc agcaactggt taagagttc     1080
ttcaatggca aggaaccatc ccgtggcata aacccagatg aagctgtagc gtatggtgct    1140
gctgtccagg ctggtgtgct ctctggtgat caagatacag gtgacctggt actgcttgat    1200
gtatgtcccc ttacacttgg tattgaaact gtgggaggtg tcatgaccaa actgattcca    1260
aggaacacag tggtgcctac caagaagtct cagatctttt ctacagcttc tgataatcaa    1320
```

-continued

```
ccaactgtta caatcaaggt ctatgaaggt gaaagacccc tgacaaaaga caatcatctt  1380
ctgggtacat ttgatctgac tggaattcct cctgctcctc gtggggtccc acagattgaa  1440
gtcacctttg agatagatgt gaatggtatt cttcgagtga cagctgaaga caagggtaca  1500
gggaacaaaa ataagatcac aatcaccaat gaccagaatc gcctgacacc tgaagaaatc  1560
gaaaggatgg ttaatgatgc tgagaagttt gctgaggaag acaaaaagct caaggagcgc  1620
attgatacta gaaatgagtt ggaaagctat gcctattctc taaagaatca gattggagat  1680
aaagaaaagc tgggaggtaa actttcctct gaagataagg agaccatgga aaaagctgta  1740
gaagaaaaga ttgaatggct ggaaagccac caagatgctg acattgaaga cttcaaagct  1800
aagaagaagg aactggaaga aattgttcaa ccaattatca gcaaactcta tggaagtgca  1860
ggccctcccc caactggtga agaggataca gcagaactcc accaccacca ccaccac     1917
```

As used herein, the term "BiP" refers to the 78 kD endoplasmic reticulum chaperone protein as disclosed in WO 00/21995. Preferably the BiP polypeptide has the amino acid sequence as shown in appendix 2 of WO00/21995 at page 23. Preferably, the BiP protein has the amino acid sequence given in WO 00/21995 as SEQ ID NO. 1 or SEQ ID NO. 2. Preferably the BiP sequences used herein are devoid of tags such as the 6His tags present in the polypeptides referred to above. As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "protein".

Preferably, the BiP protein is encoded by the nucleotide sequence given in WO 00/21995 as SEQ ID NO. 3. The nucleotide sequence may be DNA or RNA of genomic, synthetic or recombinant origin e.g. cDNA. The nucleotide sequence may be double-stranded or single-stranded whether representing the sense or antisense strand or combinations thereof. The nucleotide sequence may be prepared by use of recombinant DNA techniques (e.g. recombinant DNA). In particular, methods for the expression of BiP in *E. Coli* and purification of the recombinant protein are disclosed in WO 00/21995. The nucleotide sequence may be the same as the naturally occurring form, or may be a fragment, homologue, valiant or derivative thereof. As used herein, the term "BiP activity" refers to the level and/or pattern of BiP expression and/or activity.

Osteoclasts

As used herein, the term "osteoclast" refers to a cell that actively reabsorbs bone so that new bone may be replaced by osteoblast cells. This term encompasses at least osteoclast precursors, multi-nucleated osteoclast precursors and mature osteoclasts.

For diseases in which osteoclasts resorb bone at abnormal levels (e.g. abnormally high levels) and osteoblasts form bone at normal levels, as in, for example, musculoskeletal diseases—such as osteoporosis—the osteoclast is a therapeutic target. By way of example, the therapeutic strategy may rely on decreasing the number of osteoclasts or the resorption activity of the osteoclasts. This strategy may be used to restore the equilibrium between bone resorption and formation. In the context of the present invention the therapeutic target is the modulation (e.g. inhibition) of osteoclast development, preferably, osteoclast maturation, using BiP.

In the context of the present invention, osteoclast maturation also includes osteoclast differentiation and development, as described in the accompanying Examples. Osteoclast maturation includes, but is not limited to, the maturation (e.g. differentiation) of an osteoclast precursor or a multi-nucleated precursor into a mature osteoclast.

For a review of the role of osteoblasts and osteoclasts in bone formation and resorption processes, reference can be made to H. Fleisch, Bisphosphonates In Bone Disease, From The Laboratory To The Patient, 3rd Edition, Parthenon Publishing (1997).

By way of background information, osteoclasts are bone-resorbing cells which are involved in bone remodelling. They are multinucleated phagocytic cells, rich in the enzyme tartrate-resistant acid phosphatase, which are formed by fusion of precursors derived from the cells of monocyte/macrophage lineage. Several molecules that are of key importance in the regulation of osteoclast differentiation have been identified (*Br Med J* 1997; 315:469-472). The transcription factor PU-1 which is expressed in early osteoclast precursors is necessary for the initial stages of osteoclast and monocyte differentiation, whereas other transcription factors including c-fos and NF-κB play an essential role in stimulating differentiation of committed precursors to mature osteoclasts. Osteoclast formation and activation is also dependent on close contact between osteoclast precursors and bone marrow stromal cells. Stromal cells secrete the cytokine M-CSF, which is essential for differentiation of both osteoclasts and macrophages from a common precursor. Stromal cells also express a molecule called RANK ligand (RANKL) on the cell surface, which interacts with another cell surface receptor present on osteoclast precursors called RANK (Receptor Activator of Nuclear Factor Kappa B) to promote differentiation of osteoclast precursors to mature osteoclasts. The RANK-RANKL interaction is blocked by another molecule called Osteoprotegerin (OPG), which is a "decoy" ligand for RANK and which acts a potent inhibitor of osteoclast formation. Mature osteoclasts form a tight seal over the bone surface and resorb bone by secreting hydrochloric acid and proteolytic enzymes through the "ruffled border" into a space beneath the osteoclast (Howship's lacuna). Formation of this ruffled border is critically dependent on the presence of c-src, a cell membrane associated signalling protein. The hydrochloric acid secreted by osteoclasts dissolves hydroxyapatite and allows proteolytic enzymes (mainly Cathepsin K and matrix metalloproteinases) to degrade collagen and other matrix proteins. Molecules which have been identified as being important in regulating osteoclast activity include; carbonic anhydrase II (Ca-II) which catalyses formation of hydrogen ions within osteoclasts; TCIRG1, which encodes a subunit of the osteoclast proton pump, and Cathepsin K which degrades collagen and other non-collagenous proteins. After resorption is completed osteoclasts undergo programmed cell death (apoptosis), in the so-called reversal phase which heralds the start of bone formation.

Bone Loss

Disorders associated with or related to bone loss, include, but are not limited to, Paget's Disease, primary and secondary osteoporosis, post menopausal osteoporosis, senile osteoporosis, glucocorticoid-induced osteoporosis, periodontal disease, alveolar bone loss, post-osteotomy and childhood idiopathic bone loss, long term complications of osteoporosis—such as curvature of the spine and loss of height—and prosthetic surgery, as well as loosening of prosthetic joints such as hips, knees and the like.

Bone loss may be characterised by bone destruction, bone erosion, bone thinning or bone digestion. As will be apparent herein, this may be brought about by a pathological change in the balance between bone deposit and bone resorption.

In a further embodiment, BiP may be used in the treatment of condition(s) associated with low bone mass. Such conditions will be apparent where the level of bone mass is below the age specific normal as defined in standards by the World Health Organization Assessment of Fracture Risk and its Application to Screening for Postmenopausal Osteoporosis (1994). Report of a World Health Organization Study Group. World Health Organization Technical Series 843. The phrase "condition(s) which present with low bone mass" also refers to a vertebrate, e.g., a mammal known to have a significantly higher than average chance of developing diseases—such as osteoporosis (e.g., post-menopausal women, men over the age of 50). Other bone mass augmenting or enhancing uses may include bone restoration, increasing the bone fracture healing rate, replacing bone graft surgery entirely, enhancing the rate of successful bone grafts, bone healing following facial reconstruction or maxillary reconstruction or mandibular reconstruction, prosthetic ingrowth, vertebral synostosis or long bone extension.

In a highly preferred embodiment, BiP is used for the prevention or treatment of bone resorption. In the context of the present invention, bone resorption is prevented or treated by modulating (e.g. preventing) bone resorption by the direct or indirect alteration of osteoclast formation or activity. Bone resorption may be modulated by inhibiting the removal of existing bone either from the mineral phase and/or the organic matrix phase, through direct or indirect alteration of osteoclast formation or activity. A variety of disorders in humans and other mammals involve or are associated with abnormal bone resorption. Such disorders include, but are not limited to, osteoporosis, glucocorticoid induced osteoporosis, Paget's disease, abnormally increased bone turnover, periodontal disease, tooth loss, bone fractures, periprosthetic osteolysis, osteogenesis imperfecta, metastatic bone disease, hypercalcemia of malignancy, and multiple myeloma.

Preferably, the bone loss or bone resorption is associated with musculoskeletal disease—such as osteoporosis or Paget's disease.

Preferably, the bone loss or bone resorption underlies musculoskeletal disease—such as osteoporosis or Paget's disease.

In a highly preferred embodiment, the condition associated with bone loss or bone resorption is osteoporosis.

Osteoporosis is a major health problem in society and even though there are other diseases that result in reduction in bone mass, i.e. Paget's disease, osteoporosis is by far the most common and the disease that is the most costly in terms of health care. Since oestrogen is a hormone that regulates bone metabolism directly and indirectly, the decrease in oestrogen production in post-menopausal women and the decline with age in the production of androgen, which is enzymatically converted to oestrogen in men) is responsible for the risk of osteoporosis, which is estimated to be 85% in women and 15% in men older than 45 years of age. In osteoporosis, there is a slow-down in bone formation by osteoblasts, which occurs normally due to the aging process. One of the most unfortunate misunderstandings about osteoporosis is the widespread belief that it is almost exclusively a disease of ageing. While postmenopausal osteoporosis is one of the most common of ageing women's diseases, the process that leads to disabling bone loss begins much earlier. In fact, it has been estimated that a surprisingly large segment of the female population between the ages of 25 to 35 suffer from accelerated bone loss. As much as half of a woman's lifetime bone loss occurs before she ever begins to experience the symptoms of menopause.

Methods for treating "secondary osteoporosis" are also included within the scope of the invention. "Secondary osteoporosis" includes, but is not limited to glucocorticoid-induced osteoporosis, hyperthyroidism-induced osteoporosis, immobilization-induced osteoporosis, heparin-induced osteoporosis and immunosuppressive-induced osteoporosis in a vertebrate, e.g., a mammal (including a human being).

The presence of bone loss or bone resorption may be determined using various methods that are known in the art—such as by performing a Bone Resorption Assessment. This is a non-invasive evaluation of the biochemical markers of bone loss. It can also be used to measure the rate of bone loss long before problems can be detected using other measures—such as bone density. As the matrix framework of bone undergoes resorption—crosslinks that stabilize collagen molecules—such as deoxypyridinium (D-pyd) and/or pyridinium (Pyd)—are excreted in the urine and their levels relative to normal levels are an indication of how quickly bone is being lost.

When these markers are high, it is an indication that bone is being lost at a rate greater than the body is capable of replacing it.

Alternatively, bone loss or resorption may be determined by clinical techniques such as dual energy X-ray absorption (DEXA) scan of the spine and/or neck of the femur.

Bone growth may even be promoted in a mammal. Conditions wherein promotion of bone growth is beneficial include strengthening a bone graft, inducing vertebral synostosis, enhancing long bone extension, enhancing bone healing following facial reconstruction, maxillary reconstruction and/or mandibular reconstruction in a vertebrate, e.g., a mammal (including a human being), and the like.

Diagnosis

In a further aspect, the present invention relates to a method of diagnosing a disease or syndrome caused by or associated with bone loss or bone resorption.

In order to provide a basis for the diagnosis of disease, normal or standard levels or patterns of BiP expression and/or activity should be established. This may be accomplished by testing the levels or patterns of expression and/or activity of BiP in a sample from one or more normal subjects—such as normal animal or human subjects. The standard levels and/or patterns of expression and/or activity of BiP in the sample may be quantified by comparing it to a dilution series of positive controls where the levels or patterns of expression and/or activity of BiP are in a known amount. Then, standard values obtained from normal samples may be compared with values obtained from samples from subjects potentially affected by a disease caused by or associated with bone loss or bone resorption. Deviation between control and subject values may be used to establish the presence of a disease state. Typically, this deviation will be a decrease in the level or pattern of BiP expression and/or activity in the sample from the subject potentially affected by a disease as compared to the control.

To reach a diagnosis, it may be necessary to quantify osteoclasts and osteobalsts—especially in diseases in which osteoclasts resorb bone at abnormal levels (e.g. abnormally high levels) and osteoblasts form bone at normal levels, as in, for example, musculoskeletal diseases—such as osteoporosis. By quantifying both osteoclasts and osteoblasts, it may be possible to determine the equilibrium between bone resorption and formation and determine if a disease or syndrome associated with an imbalance between this equilibrium is present.

A BiP polynucleotide or a fragment, variant, homologue or derivative thereof may provide the basis for a diagnostic test. For diagnostic purposes, a BiP polynucleotide sequence or any part thereof may be used to detect and quantify BiP gene expression and/or activity. For example, polynucleotide sequences—such as SEQ ID No. 3 from WO 00/21995—encoding BiP may be used in hybridisation or PCR assays of samples to detect abnormalities in BiP expression. The form of such qualitative or quantitative methods may include Southern or Northern analysis, dot blot or other membrane-based technologies; PCR technologies; dip stick, pin or chip technologies; and ELISA or other multiple sample formal technologies. All of these techniques are well known in the art and are in fact the basis of many commercially available diagnostic kits.

For example, the diagnostic assay may be performed by taking a sample from a subject—such as a human. Nucleic acid—such as DNA, cDNA or RNA—is extracted from the sample. BiP expression may be detected using PCR—such as quantitative Real Time PCR (qRT-PCR). PCR primers can be designed to detect BiP. Examples of such primers are set forth in WO 00/21995.

Diagnostic assays for BiP may also include methods utilising an antibody, preferably, fused to a label, to detect the polypeptide in a sample containing, for example, body fluids, cells—such as cells from or derived from bone (e.g. osteoclasts), tissues, sections or extracts of such tissues. The polypeptides and antibodies may be used with or without modification. Frequently, the polypeptides and antibodies will be labelled by joining them, either covalently or noncovalently, with a reporter molecule. A wide variety of reporter molecules are known to those of skill in the art. BiP-specific antibodies are also useful for the diagnosis of the diseases described herein. A variety of protocols for competitive binding or immunoradiometric assays using either polyclonal or monoclonal antibodies with established specificities are well known in the art. Such immunoassays typically involve the formation of complexes between BiP and its specific antibody (or similar receptor-binding molecule) and the measurement of complex formation. The immunoassay may be two-site, monoclonal based immunoassay utilising monoclonal antibodies reactive to two non-interfering epitopes on BiP. A competitive binding assay may also be employed. Examples of such assays are described in Maddox D E et al (1983, J Exp Med 158:1211).

The diagnostic assays may even be tailored to evaluate the efficacy of a particular therapeutic treatment regime and may be used in animal studies, in clinical trials, or in monitoring the treatment of an individual patient. In order to provide a basis for the diagnosis of disease, a normal, standard or control profile for BiP expression should be established, as mentioned above. Deviation between standard and subject values establishes the presence of the disease state. If one or more disease states are established, an existing therapeutic agent may be administered, and treatment profile or values may be generated. Finally, the assay may be repeated on a regular basis to evaluate whether the values progress toward or return to the normal or standard pattern. Successive treatment profiles may be used to show the efficacy of treatment over a period of several days or several months.

Accordingly, in a further aspect there is provided a method (preferably, an in vitro method) of determining the effectiveness of at least a drug or medial regime for preventing or treating bone destruction or bone loss, said method comprising: (a) measuring the BiP activity in the presence of said drug or medial regime; and (b) at least determining if said drug or medical regime is effective in preventing or treating bone destruction or bone loss as compared to a control.

Preferably, the level or pattern of BiP expression and/or activity in subjects potentially affected by a disease caused by or associated with bone destruction or bone loss is decreased in comparison to the standard values obtained from the control.

The diagnostic method may even comprise the optional step of detecting osteoclast maturation or bone resorption.

Sample

As used herein, the term "sample" has its natural meaning. A sample may be any physical entity tested for the level and/or pattern of BiP expression and/or activity according to the methods of the present invention. A sample may be any physical entity in which osteoclast development or bone resorption is measured.

The sample may be or may be derived from biological material—such as tissues, cells (e.g. osteoclasts) or fluids. The tissues, cells or fluids may be or may be derived from bone.

The sample may be or may be derived from a biopsy or an autopsy.

Assay Method

In a further aspect, the present invention provides an assay for identifying an agent that modulates bone destruction or bone loss.

Suitably, the assay method may be used to identify one or more agents that are an antagonist of BiP that decreases, reduces or diminishes the level or pattern of expression and/or activity of BiP.

Preferably, the assay method of the present invention is used to identify one or more agents that are agonists of BiP that potentiate, enhance or increase the level and/or pattern of BiP expression and/or activity. By potentiating, enhancing or increasing the expression and/or activity of BiP, the agonist may modulate disorders associated with bone loss or bone digestion—such as bone loss or bone resorption that is associated with or a cause of osteoporosis. By potentiating, enhancing or increasing the expression and/or activity of BiP, the agonist advantageously inhibits, diminishes or decreases osteoclast maturation.

Fusion proteins, may be used for high-throughput screening assays to identify agents which modulate the activity and/or expression of BiP (see D. Bennett et al., *J Mol Recognition*, 8: 52-58 (1995); and K. Johanson et al., *J Biol Chem*, 270(16): 9459-9471 (1995)). Another technique for screening provides for high throughput screening (HTS) of agents having suitable binding affinity and is based upon the method described in detail in WO 84/03564. For a general reference on screening, see the Handbook of Drug Screening, edited by Ramakrishna Seethala, Prabhavathi B. Fernandes. New York, N.Y., Marcel Dekker, 2001 (ISBN 0-8247-0562-9).

It is expected that the assay methods of the present invention will be suitable for both small and large-scale screening of agents as well as in quantitative assays.

The screening method may measure the binding of an agent to BiP by means of a label directly or indirectly associated with the agent. Alternatively, the screening method may involve competition with a labelled competitor.

A plurality of agents may be screened.

Where the candidate compounds are proteins e.g. antibodies or peptides, libraries of candidate compounds may be screened using phage display techniques. Phage display is a protocol of molecular screening, which utilises recombinant bacteriophage. The technology involves transforming bacteriophage with a gene that encodes the library of candidate compounds, such that each phage or phagemid expresses a particular candidate compound. The transformed bacteriophage (which preferably is tethered to a solid support) expresses the appropriate candidate compound and displays it on their phage coat. Specific candidate compounds which are capable of interacting with the BiP are enriched by selection strategies based on affinity interaction. The successful candidate agents are then characterised. Phage display has advantages over standard affinity ligand screening technologies. The phage surface displays the candidate agent in a three dimensional configuration, more closely resembling its naturally occurring conformation. This allows for more specific and higher affinity binding for screening purposes.

Another method of screening a library of compounds utilises eukaryotic or prokaryotic host cells, which are stably transformed with recombinant DNA molecules expressing the library of compounds. Such cells, either in viable or fixed form, can be used for standard binding-partner assays. See also Parce et al. (1989) *Science* 246:243-247; and Owicki et al. (1990) *Proc. Nat'l Acad. Sci. USA* 87; 4007-4011, which describe sensitive methods to detect cellular responses. Competitive assays are particularly useful, where the cells expressing the library of compounds are incubated with a labelled antibody, such as $^{125}$I-antibody, and a test sample such as a candidate compound whose binding affinity to the binding composition is being measured. The bound and free labelled binding partners are then separated to assess the degree of binding. The amount of test sample bound is inversely proportional to the amount of labelled antibody bound.

Any one of numerous techniques can be used to separate bound from free binding partners to assess the degree of binding. This separation step could typically involve a procedure such as adhesion to filters followed by washing, adhesion to plastic following by washing, or centrifugation of the cell membranes.

Another technique for candidate compound screening involves an approach, which provides high throughput screening for new compounds having suitable binding affinity and is described in detail in WO 84/03564. First, large numbers of different small peptide agents are synthesised on a solid substrate, e.g., plastic pills or some other appropriate surface. Then all the pins are reacted with solubilised protein and washed. The next step involves detecting bound protein. Detection may be accomplished using a monoclonal antibody. Compounds which interact specifically with the protein may thus be identified.

Rational design of candidate compounds likely to be able to interact with BiP may be based upon structural studies of the molecular shapes of the protein and/or its in vivo binding partners. One means for determining which sites interact with specific other proteins is a physical structure determination, e.g., X-ray crystallography or two-dimensional NMR techniques. These will provide guidance as to which amino acid residues form molecular contact regions. For a detailed description of protein structural determination, see, e.g., Blundell and Johnson (1976) Protein Crystallography, Academic Press, New York.

Once an agent which modulates the activity and/or expression of BiP has been identified, osteoclast maturation or bone resorption in the presence of said agent may be measured using, for example, the methods described herein. A difference between a) osteoclast maturation or bone resorption in the absence of the agent and b) osteoclast maturation or bone resorption in the presence of the agent is indicative that the agent can modulate bone destruction.

Preferably, the difference is a decrease or an inhibition of osteoclast maturation in the presence of the agent.

Preferably, the difference is a decrease or an inhibition of bone resorption in the presence of the agent.

By way of example only, osteoclast maturation or bone resorption may be assessed using pulse studies, where BiP is added during, for example, the early stages of precursor differentiation, or after formation of multinucleated cells. At the appropriate time, cultures are fixed and stained histochemically for e.g. TRAP activity or stained for VnR and F-actin rings by immunolocalisation using an antibody—such as the 23C6 antibody (e.g. catalogue number 14-0519 from eBioscience Inc.), and TRITC-phalloidin, respectively, and the number of osteoclasts quantified. Resorption may be quantified following removal of osteoclasts from dentine slices and staining with toluidine blue. Additional confirmation of osteoclast differentiation may be confirmed by molecular techniques—such as real-time PCR to measure the expression of osteoclast-specific marker genes—such as calcitonin receptor and cathepsin K.

Modulating

In the context of BiP and the modulation of bone resorption and maturation of osteoclasts, the term "modulating" preferably refers to preventing, suppressing, alleviating, decreasing, inhibiting or preventing bone resorption and maturation of osteoclasts using BiP.

Accordingly, the present invention relates to inter alia assay methods, processes, and agents that modulate or affect the modulation of the level and/or pattern of BiP expression and/or activity. By way of example, if the level and/or pattern of BiP expression and/or activity is prevented, suppressed, alleviated, decreased, inhibited or prevented then osteoclast maturation and bone resorption is restored, elevated or increased. Preferably, the level and/or pattern of BiP expression and/or activity is restored, elevated or increased and so osteoclast maturation and bone resorption is prevented, suppressed, alleviated, decreased, inhibited or prevented.

Agent

The agent may be an organic compound or other chemical. The agent may be a compound, which is obtainable from or produced by any suitable source, whether natural or artificial. The agent may be an amino acid molecule, a polypeptide, or a chemical derivative thereof, or a combination thereof. The agent may even be a polynucleotide molecule—which may be a sense or an anti-sense molecule, or an antibody, for example, a polyclonal antibody, a monoclonal antibody or a monoclonal humanised antibody.

Various strategies have been developed to produce monoclonal antibodies with human character, which bypasses the need for an antibody-producing human cell line. For example, useful mouse monoclonal antibodies have been "humanised" by linking rodent variable regions and human constant regions (Winter, G. and Milstein, C. (1991) *Nature* 349, 293-299). This reduces the human anti-mouse immunogenicity of the antibody but residual immunogenicity is retained by virtue of the foreign V-region framework. Moreover, the antigen-binding specificity is essentially that of the murine donor. CDR-grafting and framework manipulation (EP 0239400) has improved and refined antibody manipulation to the point where it is possible to produce humanised murine antibodies which are acceptable for therapeutic use in humans. Humanised antibodies may be obtained using other methods well known in the art (for example as described in U.S. Pat. No. 239,400).

The agents may be attached to an entity (e.g. an organic molecule) by a linker which may be a hydrolysable bifunctional linker.

The entity may be designed or obtained from a library of compounds, which may comprise peptides, as well as other compounds, such as small organic molecules.

By way of example, the entity may be a natural substance, a biological macromolecule, or an extract made from biological materials such as bacteria, fungi, or animal (particularly mammalian) cells or tissues, an organic or an inorganic molecule, a synthetic agent, a semi-synthetic agent, a structural or functional mimetic, a peptide, a peptidomimetics, a peptide cleaved from a whole protein, or a peptides synthesised synthetically (such as, by way of example, either using a peptide synthesizer or by recombinant techniques or combinations thereof, a recombinant agent, an antibody, a natural or a non-natural agent, a fusion protein or equivalent thereof and mutants, derivatives or combinations thereof.

Typically, the entity will be an organic compound. For some instances, the organic compounds will comprise two or more hydrocarbyl groups. Here, the term "hydrocarbyl group" means a group comprising at least C and H and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. For some applications, preferably the entity comprises at least one cyclic group. The cyclic group may be a polycyclic group, such as a non-fused polycyclic group. For some applications, the entity comprises at least the one of said cyclic groups linked to another hydrocarbyl group.

The entity may contain halo groups—such as fluoro, chloro, bromo or iodo groups.

The entity may contain one or more of alkyl, alkoxy, alkenyl, alkylene and alkenylene groups—which may be unbranched- or branched-chain.

As described above, the agent may be an antibody.

Procedures well known in the art may be used for the production of antibodies to BiP. Such antibodies include, but are not limited to, polyclonal, monoclonal, chimeric, single chain, Fab fragments and fragments produced by a Fab expression library. Neutralising antibodies, i.e., those which may modulate the biological activity BiP, are especially preferred for diagnostics and therapeutics.

For the production of antibodies, various hosts including goats, rabbits, rats, mice, etc. may be immunised by injection with one or more of the polypeptides described herein or any portion, variant, homologue, fragment or derivative thereof or oligopeptide which retains immunogenic properties. Depending on the host species, various adjuvants may be used to increase immunological response. Such adjuvants include, but are not limited to, Freund's, mineral gels—such as aluminium hydroxide—and surface active substances—such as lysolecithin, pluronic polyols, polyanions, peptides, oil emulsions, keyhole limpet hemocyanin, and dinitrophenol. BCG (*Bacilli Calmette-Guerin*) and *Corynebacterium parvum* are potentially useful human adjuvants which may be employed.

Preferably, the antibody is a monoclonal antibody.

Monoclonal antibodies may be prepared using any technique which provides for the production of antibody molecules by continuous cell lines in culture. These include, but are not limited to, the hybridoma technique originally described by Koehler and Milstein (1975 Nature 256:495-497), the human B-cell hybridoma technique (Kosbor et al (1983) Immunol Today 4:72; Cote et al (1983) Proc Natl Acad Sci 80:2026-2030) and the EBV-hybridoma technique (Cole et al (1985) Monoclonal Antibodies and Cancer Therapy, Alan R Liss Inc, pp 77-96). In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851-6855; Neuberger et al (1984) Nature 312:604-608; Takeda et al (1985) Nature 314:452-454). Alternatively, techniques described for the production of single chain antibodies (U.S. Pat. No. 4,946,779) can be adapted to produce inhibitor specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833-3837), and Winter G and Milstein C (1991; Nature 349:293-299).

Antibody fragments which contain specific binding sites for BiP may also be generated. For example, such fragments include, but are not limited to, the $F(ab')_2$ fragments which can be produced by pepsin digestion of the antibody molecule and the Fab fragments which can be generated by reducing the disulphide bridges of the $F(ab')_2$ fragments. Alternatively, Fab expression libraries may be constructed to allow rapid and easy identification of monoclonal Fab fragments with the desired specificity (Huse W D et al (1989) Science 256:1275-1281).

An alternative technique involves screening phage display libraries where, for example the phage express scFv fragments on the surface of their coat with a large variety of complementarity determining regions (CDRs). This technique is well known in the art.

Preferably, the antibody is a humanised antibody.

Humanised antibodies have been obtained by replacing the constant region of a mouse antibody with human protein, but by also replacing portions of the antibody's variable region with human protein. Generally humanised antibodies are 5-10% mouse and 90-95% human. Humanised antibodies were developed to counter the immune responses seen with murine and chimeric antibodies. Data from humanised antibodies used in clinical trials show that humanised antibodies exhibit minimal or no response of the human immune system against them.

A more sophisticated approach to humanised antibodies involves not only providing human-derived constant regions, but also modifying the variable regions as well. This allows the antibodies to be reshaped as closely as possible to the human form. The variable regions of both heavy and light chains contain three complementarity-determining regions (CDRs) which vary in response to the antigens in question and determine binding capability, flanked by four framework regions (FRs) which are relatively conserved in a given species and which putatively provide a scaffolding for the CDRs.

When non-human antibodies are prepared with respect to a particular antigen, the variable regions can be "reshaped" or "humanised" by grafting CDRs derived from nonhuman antibody on the FRs present in the human antibody to be modified. This approach has been reported in, for example, Cancer Res (1993) 53:851-856, Nature (1988) 332:323-327, Science (1988) 239:1534-1536, Proc Natl Acad Sci USA (1991) 88:4181-4185 and J Immunol (1992) 148:1149-1154.

In accordance with the present invention, the agent may bind to the nucleotide sequence encoding BiP, or control regions associated with the nucleotide coding sequence, or its corresponding RNA transcript to modulate (e.g. increase) the rate of transcription or translation of BiP. For example, the expression of BiP may be modulated by modulating the transcription of BiP mRNA, or by modulating mRNA processing etc. Translation of BiP from BiP mRNA may also be regulated as a means of modulating the expression of the protein. Such modulation may make use of methods known in the art, for example, by use of agents that affect transcription or translation.

Such agents may even modulate the activity of a further entity.

It is especially preferred that the agent, increases, enhances or upregulates the expression and/or activity of BiP. In this respect, the agent may be a regulatory sequence—such as a promoter or an enhancer—that increases, enhances or up regulates the expression of BiP, inserted for example, via homologous recombination. Preferably, following insertion of the regulatory sequence, BiP and the regulatory sequence are operably linked. A regulatory sequence "operably linked" to a BiP coding sequence is ligated in such a way that expression of the coding sequence is achieved under conditions compatible with the control sequences.

Prodrug

It will be appreciated by those skilled in the art that the entity may be derived from a prodrug. Examples of prodrugs include certain protected group(s) which may not possess pharmacological activity as such, but may, in certain instances, be administered (such as orally or parenterally) and thereafter metabolised in the body to form an entity that is pharmacologically active.

Suitable pro-drugs may include, but are not limited to, Doxorubicin, Mitomycin, Phenol Mustard, Methotraxate, Antifolates, Chloramphenicol, Camptothecin, 5-Fluorouracil, Cyanide, Quinine, Dipyridamole and Paclitaxel. Agents (e.g. an antibody or a fragment thereof) may be chemically linked to an enzyme of interest. Alternatively, the conjugate can be a fusion protein produced by recombinant DNA techniques with the antibody variable region genes and the gene encoding the enzyme.

Preferably, the prodrug should be non-toxic, resistant to the action of endogenous enzymes, and be converted into active drug only by the targeted enzyme. The selective activation of anticancer prodrugs by mAb-enzyme conjugates is reviewed in Senetr & Springer (2001) *Advanced Drug Delivery Reviews* 53, 247-264.

It will be further appreciated that certain moieties known as "pro-moieties", for example as described in "Design of Prodrugs" by H. Bundgaard, Elsevier, 1985, may be placed on appropriate functionalities of the agents. Such prodrugs are also included within the scope of the invention.

The agent may be in the form of a pharmaceutically acceptable salt—such as an acid addition salt or a base salt—or a solvate thereof, including a hydrate thereof. For a review on suitable salts see Berge et al, J. Pharm. Sci., 1977, 66, 1-19.

The agent of the present invention may be capable of displaying other therapeutic properties.

The agent may be used in combination with one or more other pharmaceutically active agents.

If combinations of active agents are administered, then the combinations of active agents may be administered simultaneously, separately or sequentially.

Stereo and Geometric Isomers

The entity may exist as stereoisomers and/or geometric isomers—e.g. the entity may possess one or more asymmetric and/or geometric centres and so may exist in two or more stereoisomeric and/or geometric forms. The present invention contemplates the use of all the individual stereoisomers and geometric isomers of those entities, and mixtures thereof.

Pharmaceutical Salt

The agents of the present invention may be administered in the form of a pharmaceutically acceptable salt.

Pharmaceutically-acceptable salts are well known to those skilled in the art, and for example, include those mentioned by Berge et al, in *J. Pharm. Sci.*, 66, 1-19 (1977). Suitable acid addition salts are formed from acids which form non-toxic salts and include the hydrochloride, hydrobromide, hydroiodide, nitrate, sulphate, bisulphate, phosphate, hydrogenphosphate, acetate, trifluoroacetate, gluconate, lactate, salicylate, citrate, tartrate, ascorbate, succinate, maleate, fumarate, gluconate, formate, benzoate, methanesulphonate, ethanesulphonate, benzenesulphonate and p-toluenesulphonate salts.

When one or more acidic moieties are present, suitable pharmaceutically acceptable base addition salts can be formed from bases which form non-toxic salts and include the aluminium, calcium, lithium, magnesium, potassium, sodium, zinc, and pharmaceutically-active amines such as diethanolamine, salts.

A pharmaceutically acceptable salt of an agent may be readily prepared by mixing together solutions of the agent and the desired acid or base, as appropriate. The salt may precipitate from solution and be collected by filtration or may be recovered by evaporation of the solvent.

The agent may exist in polymorphic form.

The agent of the present invention may contain one or more asymmetric carbon atoms and therefore exists in two or more stereoisomeric forms. Where an agent contains an alkenyl or alkenylene group, cis (E) and trans (Z) isomerism may also occur. The present invention includes the individual stereoisomers of the agent and, where appropriate, the individual tautomeric forms thereof, together with mixtures thereof.

Separation of diastereoisomers or cis and trans isomers may be achieved by conventional techniques, e.g. by fractional crystallisation, chromatography or H.P.L.C. of a stereoisomeric mixture of the agent or a suitable salt or derivative thereof. An individual enantiomer of the agent may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

The agent may also include all suitable isotopic variations of the agent or a pharmaceutically acceptable salt thereof. An isotopic variation of an agent or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^{2}H$, $^{3}H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^3$H or $^{14}$C is incorporated, are useful in drug and/or substrate tissue distribution studies. Tritiated, i.e., $^3$H, and carbon-14, i.e., $^{14}$C, isotopes are particularly preferred for their ease of preparation and detectability. Further, substitution with isotopes such as deuterium, i.e., $^2$H, may afford certain therapeutic advantages resulting from greater metabolic stability, for example, increased in vivo half-life or reduced dosage requirements and hence may be preferred in some circumstances. Isotopic variations of the agent and pharmaceutically acceptable salts thereof of this invention can generally be prepared by conventional procedures using appropriate isotopic variations of suitable reagents.

Pharmaceutically Active Salt

The agent may be administered as a pharmaceutically acceptable salt. Typically, a pharmaceutically acceptable salt may be readily prepared by using a desired acid or base, as appropriate. The salt may precipitate from solution and be collected by filtration or may be recovered by evaporation of the solvent.

Chemical Synthesis Methods

The agent may be prepared by chemical synthesis techniques.

It will be apparent to those skilled in the art that sensitive functional groups may need to be protected and deprotected during synthesis of a compound of the invention. This may be achieved by conventional techniques, for example, as described in "Protective Groups in Organic Synthesis" by T W Greene and P G M Wuts, John Wiley and Sons Inc. (1991), and by P. J. Kocienski, in "Protecting Groups", Georg Thieme Verlag (1994).

It is possible during some of the reactions that any stereocentres present could, under certain conditions, be racemised, for example, if a base is used in a reaction with a substrate having an having an optical centre comprising a base-sensitive group. This is possible during e.g. a guanylation step. It should be possible to circumvent potential problems such as this by choice of reaction sequence, conditions, reagents, protection/deprotection regimes, etc. as is well-known in the art.

The compounds and salts may be separated and purified by conventional methods.

Separation of diastereomers may be achieved by conventional techniques, e.g. by fractional crystallisation, chromatography or H.P.L.C. of a stereoisomeric mixture of a compound of formula (I) or a suitable salt or derivative thereof. An individual enantiomer of a compound of formula (I) may also be prepared from a corresponding optically pure intermediate or by resolution, such as by H.P.L.C. of the corresponding racemate using a suitable chiral support or by fractional crystallisation of the diastereomeric salts formed by reaction of the corresponding racemate with a suitably optically active acid or base.

The agent or variants, homologues, derivatives, fragments or mimetics thereof may be produced using chemical methods to synthesise the agent in whole or in part. For example, if the agent comprises a peptide, then the peptide can be synthesised by solid phase techniques, cleaved from the resin, and purified by preparative high performance liquid chromatography (e.g., Creighton (1983) Proteins Structures And Molecular Principles, WH Freeman and Co, New York N.Y.). The composition of the synthetic peptides may be confirmed by amino acid analysis or sequencing (e.g., the Edman degradation procedure; Creighton, supra).

Synthesis of peptide inhibitor agents (or variants, homologues, derivatives, fragments or mimetics thereof) can be performed using various solid-phase techniques (Roberge JY et al (1995) Science 269: 202-204) and automated synthesis may be achieved, for example, using the ABI 43 1 A Peptide Synthesizer (Perkin Elmer) in accordance with the instructions provided by the manufacturer. Additionally, the amino acid sequences comprising the agent, may be altered during direct synthesis and/or combined using chemical methods with a sequence from other subunits, or any part thereof, to produce a variant agent.

Chemical Derivative

The term "derivative" or "derivatised" as used herein includes chemical modification of an agent. Illustrative of such chemical modifications would be replacement of hydrogen by a halo group, an alkyl group, an acyl group or an amino group.

Chemical Modification

The agent may be a modified agent—such as, but not limited to, a chemically modified agent.

The chemical modification of an agent may either enhance or reduce hydrogen bonding interaction, charge interaction, hydrophobic interaction, Van Der Waals interaction or dipole interaction.

In one aspect, the agent may act as a model (for example, a template) for the development of other compounds.

Pharmaceutical Compositions

Pharmaceutical compositions of the present invention may comprise a therapeutically effective amount of an agent.

Pharmaceutical compositions of the present invention may comprise a therapeutically effective amount of BiP.

Pharmaceutical compositions of the present invention may comprise a therapeutically effective amount of an agent and BiP.

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be administered using a mini-pump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be administered by a number of routes.

If the agent is to be administered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions may be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or the pharmaceutical compositions can be injected parenterally, for example, intravenously, intramuscularly or subcutaneously. For parenteral administration, the compositions may be best used in the form of a sterile aqueous solution which may contain other substances, for example, enough salts or monosaccharides to make the solution isotonic with blood. For buccal or sublingual administration the compositions may be administered in the form of tablets or lozenges which can be formulated in a conventional manner.

The agents may be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

If the agent is a protein, then said protein may be prepared in situ in the subject being treated. In this respect, nucleotide sequences encoding said protein may be delivered by use of non-viral techniques (e.g. by use of liposomes) and/or viral techniques (e.g. by use of retroviral vectors) such that the said protein is expressed from said nucleotide sequence, as described below.

Administration

As used herein the term "administration" includes delivery by viral or non-viral techniques.

Non-viral delivery mechanisms include, but are not limited to transfection, lipid mediated transfection, liposomes, immunoliposomes, lipofectin, cationic facial amphiphiles (CFAs) and combinations thereof.

Physical injection of nucleic acid into cells represents the simplest gene delivery system (Vile & Hart (1994) Ann. Oncol, suppl. 5, 59). Accordingly, vectors comprising nucleotide sequences may be administered directly as "a naked nucleic acid construct" and may further comprise flanking sequences homologous to the host cell genome. After injection, nucleic acid is taken into cells and translocated to the nucleus, where it may be expressed transiently from an episomal location or stably if integration into the host genome has occurred. The gene encoding BiP may be placed under the control of promoters. Physical interventions may increase transfection efficiency, for example, focused ultrasound. The efficiency of transfection of cells in vivo may be increased by injecting DNA coated gold particles with a gene gun (Fyan et al. (1993) *Proc. Natl. Acad. Sci. USA* 90, 11478).

Liposomes are vesicles composed of phospholipid bilayer membranes that can enclose various substances, including nucleic acid. Mixtures of lipids and nucleic acid form complexes (lipoplexes) that can transfect cells in vitro and in vivo. Lipid mediated gene delivery has the ability to transfect various different cells without the need for interaction with specific receptors, minimal immunogenicity of the lipid components to facilitate multiple administration, high capacity vectors with the ability to deliver large DNA sequences and ease of production. The insertion of polyethylene glycol derivatives into the lipid membrane or pegylation may increase the circulation half-life of liposomes after administration. The pharmacokinetics, biodistribution and fusogenicity of liposomes may be varied by altering the composition of the lipid membrane. In particular, the incorporation of certain cationic lipids, for example, DMRIE, DOSPA and DOTAP with neutral or helper co-lipids—such as cholesterol or DOPE—in liposomes may increase their ability to fuse with cell membranes and deliver their contents into cells.

A number of nonlipid polycationic polymers form complexes with nucleic acid which promotes delivery into cells (Li and Huang (2000) *Gene Ther.* 7, 31). Preferably, the nonlipid polycationic polymers include but are not limited to poly-L-lysine, polyethylenimine, polyglucosamines and peptoids. Polyethylenimine may protect complexed nucleic acids from degradation within endosomes and it also provides a means of promoting nucleic acid release from the endosomal compartment and its subsequent translocation to the nucleus (Boussif et al. (1995) *Proc. Natl. Acad. Sci. USA* 92, 7297). Pegylated polyethylenimine polymers may decrease the interaction with serum proteins, extended circulation half-life and may deliver genes to cells without significant toxicity.

The transplantation of cells, for example, autologous, allogeneic and xenogeneic cells, that are genetically engineered to release biotherapeutic molecules may also be used. The transplanted cells may be surrounded with a permselective membrane that fully contains and protects them from attack by the host immune system. This method of encapsulation allows the neural transplantation of primary cells or cell lines from both allogeneic and xenogeneic sources. Various types of encapsulation techniques are known in the art. The method of microencapsulation allows the entrapment of small cell clusters within a thin, spherical, semipermeable membrane typically made of polyelectrolytes.

Viral delivery mechanisms are attractive vehicles for gene delivery since they have evolved specific and efficient means of entering human cells and expressing their genes. Preferably, the viral genome is modified to remove sequences required for viral replication and pathogenicity. More preferably, the viral coding sequences are replaced with exogenous genes—such as BiP.

Viral delivery mechanisms include but are not limited to retrovirus, adenovirus, adeno-associated virus, herpes simplex virus, pox virus, lentiviral vectors, baculovirus, reovirus, Newcastle disease virus, alphaviruse and vesicular stomatitis virus vectors.

Retroviruses are single strand, diploid RNA viruses, which enter cells by binding surface envelope proteins, encoded by the env gene. After entering a cell, reverse transcriptase encoded by the pol gene transcribes the viral genome into a double strand DNA copy that can enter the nucleus of dividing cells and integrate randomly into the host genome. Preferably, retroviruses used for viral delivery are manipulated to render them replication deficient by removing their gag, pol and env genes. Thus, infectious but non-replicative retrovirus particles are produced in packaging cell lines that express retrovirus gag, pol and env genes from plasmids lacking a packaging sequence.

The lentiviruses, a subtype of retroviruses, may represent an alternative to retroviruses. Lentiviruses, such as HIV, simian and feline immunodeficiency viruses, can infect non-dividing cells and integrate in the same way as other retroviruses. Replication defective and multiply attenuated lentiviral vectors have been shown to lead to long term expression of various transgenes in the CNS of both rodents and primates (Bensadoun et al. (2000) *Exp. Neurol.* 164, 15-24; Kordower et al. (2000) *Exp. Neurol.* 160, 1-16). Lentiviral vectors diffuses 2-3 mm from the injection site which allows the transduction of a significant number of neurones with a sustained gene expression up to at least one year.

Still other viruses are adenoviruses, which comprise double strand DNA viruses. More than 40 adenovirus serotypes in 6 groups (A to F) have been identified. Group C viruses (serotypes Ad2 and Ad5) have been most extensively evaluated as candidates for gene delivery (Zhang (1999) *Cancer Gene Ther.* 6, 11). Adenoviruses enter cells by binding to the coxsackievirus and adenovirus receptor, which facilitates interaction of viral arginine-glycine-aspartate (RGD) sequences with cellular integrins. After internalisation, the virus escapes from cellular endosomes, partially disassembles and translocates to the nucleus, where viral gene expression begins. Preferably, the adenovirus is incapable of replication. This may be achieved by deleting one or more of the adenovirus genes—such as the early adenovirus genes E1 to E4. This may be extended to remove the whole coding sequence of the adenovirus genome. Such viruses may be used for packaging BiP genes but must be grown in producer cell lines in the presence of helper viruses that supply all necessary viral gene functions to facilitate the packaging of infectious, replication incompetent adenovirus containing the BiP gene.

Adeno-associated viruses are single strand DNA viruses that are native human viruses not known to cause any disease. They enter cells via binding to heparan sulphate but require co-infection with a so-called helper virus—such as adenovirus or herpes virus—to replicate. Adeno-associated virus vectors have a number of potential advantages. They infect non-dividing cells and are stably integrated and maintained in the host genome; integration occurs preferentially at a site dependent locus in chromosome 19, decreasing the risk of insertional mutagenesis. However, in adeno-associated virus vectors this characteristic integration is lost due to deletion of rep proteins in an attempt to decrease the risk of the emergence of replication competent adeno-associated viruses.

Herpes simplex viruses are large viruses with a linear double strand DNA genome of approximately 150 kbp that encodes more than 70 viral proteins. These viruses enter cells by binding viral glycoproteins to cell surface heparan sulfate residues. Preferably, herpes simplex viruses are rendered replication defective by inactivating a small number of genes—such as the immediate early genes ICPD, ICP4, 10P22 and ICP27. Since a large number of herpes simplex virus genes can be deleted without affecting the ability to produce viral vectors, large nucleic acid sequences containing multiple genes and their regulatory elements may be packaged within herpes simplex virus vectors.

Pox viruses are double strand DNA viruses that include vaccinia and canarypox or ALVAC. Preferably, the pox virus is a recombinant pox virus containing the BiP gene.

The components may be administered alone but will generally be administered as a pharmaceutical composition—e.g. when the components are is in admixture with a suitable pharmaceutical excipient, diluent or carrier selected with regard to the intended route of administration and standard pharmaceutical practice.

For example, the components can be administered in the form of tablets, capsules, ovules, elixirs, solutions or suspensions, which may contain flavouring or colouring agents, for immediate-, delayed-, modified-, sustained-, pulsed- or controlled-release applications.

If the pharmaceutical is a tablet, then the tablet may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

The routes for administration (delivery) may include, but are not limited to, one or more of oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, vaginal, epidural, sublingual.

Dose Levels

Typically, a physician will determine the actual dosage which will be most suitable for an individual subject. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. This amount can be determined by routine experimentation and is within the judgement of the clinician. Generally, an effective dose will be from 0.01 mg/kg to 50 mg/kg, more preferably, 0.01 mg/kg to 40 mg/kg; more preferably, 0.01 mg/kg to 30 mg/kg, more preferably, 0.01 mg/kg to 20 mg/kg, more preferably, 0.01 mg/kg to 10 mg/kg most preferably 0.05 mg/kg to 10 mg/kg.

Formulation

The component(s) may be formulated into a pharmaceutical composition, such as by mixing with one or more of a suitable carrier, diluent or excipient, by using techniques that are known in the art.

Fragments/Variants/Homologues/Derivatives

The present invention encompasses the use of fragments, variants, homologues, and derivatives of BiP.

The term "variant" is used to mean a naturally occurring polypeptide or nucleotide sequences which differs from a wild-type sequence.

The term "fragment" indicates that a polypeptide or nucleotide sequence comprises a fraction of a wild-type sequence. It may comprise one or more large contiguous sections of sequence or a plurality of small sections. The sequence may also comprise other elements of sequence, for example, it may be a fusion protein with another protein. Preferably the sequence comprises at least 50%, more preferably at least 65%, more preferably at least 80%, most preferably at least 90% of the wild-type sequence.

The term "homologue" means an entity having a certain homology with the subject amino acid sequences and the subject nucleotide sequences. Here, the term "homology" can be equated with "identity".

In the present context, a homologous sequence is taken to include an amino acid sequence, which may be at least 75, 85 or 90% identical, preferably at least 95, 96, 97 or 98% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence, which may be at least 75, 85 or 90% identical, preferably at least 95, 96, 97 or 98% identical to the subject sequence. Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons may be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, *Nucleic Acids Research* 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However, for some applications, it is preferred to use the GCG Bestfit program. A new tool, called BLAST 2 Sequences is also available for comparing protein and nucleotide sequence (see FEMS Microbiol Lett 1999 174(2): 247-50; FEMS Microbiol Lett 1999 177(1): 187-8).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix—such as BLOSUM62.

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues, which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example, according to the Table below. Amino acids in the same block in the second column and preferably in the same line in the third column may be substituted for each other:

| ALIPHATIC | Non-polar | G A P |
|---|---|---|
|  |  | I L V |
|  | Polar-uncharged | C S T M |
|  |  | N Q |
|  | Polar-charged | D E |
|  |  | K R |
| AROMATIC |  | H F W Y |

The present invention also encompasses homologous substitution (substitution and replacement are both used herein to mean the interchange of an existing amino acid residue, with an alternative residue) may occur i.e. like-for-like substitution—such as basic for basic, acidic for acidic, polar for polar etc. Non-homologous substitution may also occur i.e. from one class of residue to another or alternatively involving the inclusion of unnatural amino acids—such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids—such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid-, L-ϵ-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe)—such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid# and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups—such as methyl, ethyl or propyl groups—in addition to amino acid spacers—such as glycine or β-alanine residues. A further form of variation involves the presence of one or more amino acid residues in peptoid form will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example, Simon R J et al., PNAS (1992) 89(20), 9367-9371 and Horwell D C, Trends Biotechnol. (1995) 13(4), 132-134.

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences may be modified by any method available in the art. Such modifications may be carried out to enhance the in vivo activity or life span of nucleotide sequences useful in the present invention.

Preferably, the fragment is a functional fragment. As used herein, the term "functional fragment" refers to a fragment of BiP which is capable of eliciting at least part of an activity of the full length BiP protein. In particular, the functional fragment may have at least one of the following functions: causes CD14+ cells to release IL-10; stimulates CD8+ cells to proliferate and release IL-10; inhibits the recall antigen response; activates the expression of an array of anti-inflammatory genes in monocytes, including the migration inhibitory factor (MIF), the soluble TNF receptor II and TIMPs; inhibit oestoclast maturation; inhibit bone resorption.

Preferably, the functional fragment is at least 20 amino acids, more preferably at least 50 amino acids and most preferably at least 100 amino acids in length. Particularly preferred fragments comprise a conserved region which has been found to be homologous to a number of naturally occurring BiP proteins. Such conserved regions are considered to have a specific function.

The term "functional homologue" as used herein refers to a homologue that retains at least part of an activity of the full length BiP protein. In particular, it is preferred that the functional homologue has at least one of the following functions: causes CD14+ cells to release IL-10; stimulates CD8+ cells to proliferate and release IL-10; inhibits the recall antigen response; or activates the expression of an array of anti-inflammatory genes in monocytes, including the migration inhibitory factor (MIF), the soluble TNF receptor II and TIMPs; inhibits oestoclast maturation; inhibits bone resorption.

Gene Therapy

The present invention further relates to gene therapy whereby nucleotide sequences coding for BiP are regulated in vivo. For example, regulation of expression may be accomplished by administering agents that bind to the nucleotide coding sequence, or control regions associated with the nucleotide coding sequence for BiP, or its corresponding RNA transcript to modify, preferably, increase the rate of transcription or translation.

By way of example, a nucleotide sequence encoding BiP may be under the control of a homologous or heterologous expression regulatory element—such as a promoter or a promoter and enhancer. The enhancer and/or promoter may even be active in particular tissues, such that the nucleotide sequence coding for BiP is preferentially expressed. The enhancer element or other elements conferring regulated expression may be present in multiple copies. Likewise, or in addition, the enhancer and/or promoter may be preferentially active in one or more cell types—such as one or more cell types of bone, e.g. osteoclasts.

The level of expression of the nucleotide sequence coding, may be modulated by manipulating the promoter region. For example, different domains within a promoter region may possess different gene regulatory activities. The roles of these different regions are typically assessed using vector constructs having different variants of the promoter with specific regions deleted (that is, deletion analysis).

General Recombinant DNA Methodology Techniques

The present invention employs, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA* Methods in Enzymology, Academic Press. Each of these general texts is herein incorporated by reference.

Further Applications

Preferably the invention is applied to prevention or inhibition of osteoclast development and/or osteoclast function.

The invention will now be further described by way of Examples, which are meant to serve to assist one of ordinary skill in the art in carrying out the invention and are not intended in any way to limit the scope of the invention.

EXAMPLES

Example 1

BiP Stimulation Induces an Anti-Inflammatory Gene Activation Profile in Monocytes

Introduction

BiP, or glucose-regulated protein 78 (grp78) is an endoplasmic reticulum (ER) chaperone functionally responsible for the correct folding of proteins. Upregulation of BiP is induced when the function of the ER is disturbed, by glucose starvation, hypoxia or reactive oxygen species, causing an accumulation of unfolded proteins. These are also factors prevalent in the inflamed joint that influence the pathogenesis of rheumatoid arthritis (RA).

We isolated and identified BiP as an autoantigen in RA by using proteomics. Subsequently we showed that mononuclear cells (MC) isolated from synovial fluid (SF) of patients with RA proliferated in the presence of recombinant human (rhu) BiP, in contrast to RA peripheral blood (PB) MC and both PB and SFMC from OIJD. These cells produced little or no IFNγ. Cytokine analysis of supernatants from PBMC stimulated by BiP showed high concentrations of IL-10 and little TNFα, IFNγ, and IL-1β and no IL-2 or IL-15.

In animal models of RA prior immunisation with BiP was shown both to prevent the onset of collagen-induced arthritis (CIA) in mice. Either intravenous or sub-cutaneous administration of BiP was also therapeutic for mice in the early stages of CIA.

To investigate the mechanism of action of BiP further in vitro studies were undertaken to analyse the cytokine profile of purified monocytes stimulated with rhu BiP by two different gene array techniques.

Methods

Monocytes were purified by negative isolation using immunomagnetic beads. Total RNA was isolated from these cells which were either unstimulated or stimulated with BiP (20 μg/ml) for 24 hours. The RNA was then used in the Affymetrix gene array (U95 version2) or R&D cytokine gene array according to the manufacturer's instructions. Duplicate samples from a subject were used in the Affymetrix array and for two normal control subjects in the R&D gene array.

Results

Figure 6:
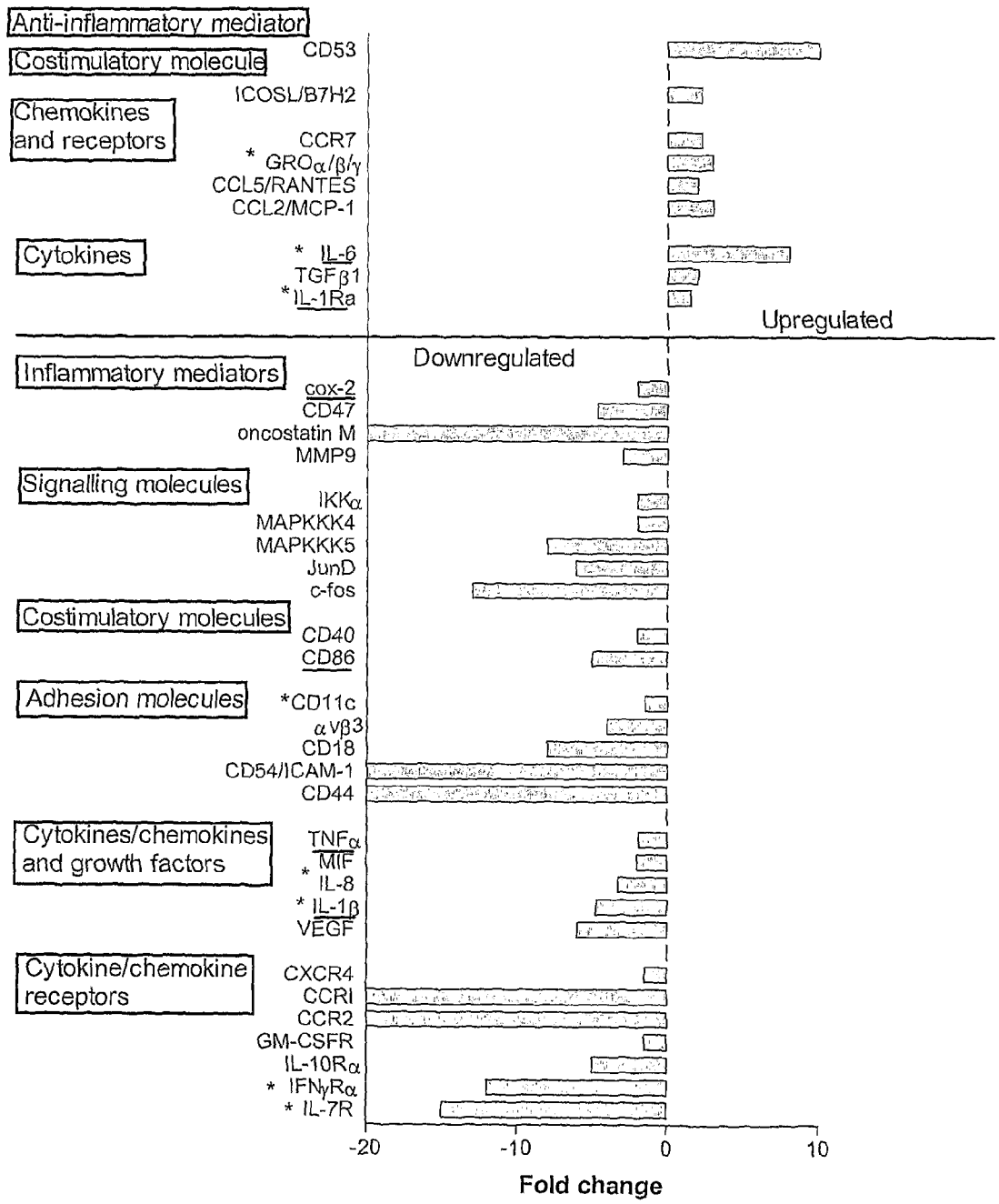

The results are shown in Table 1 and FIG. 6.

Conclusion

BiP induced the downregulation many genes activated in monocyes in the inflammatory response. These include those involved in antigen presentation, adhesion and cell migration, cell signalling and osteoclast differentiation. There was agreement between the results found using the R&D cytokine gene activation array and the Affymetrix array.

Overall these changes in monocyte gene activation induced an anti-inflammatory profile Summary BiP has been shown to bind to human monocytes via a receptor-like molecule, which is unlike those used by HSP60 or 70 and grp94. In order to investigate the consequence of BiP activation of monocytes two kinds of gene array were used.

A limited gene array of 375 cytokine/chemokine and their receptors was carried out on monocytes (unstimulated or BiP stimulated for 24 h) from two normal individuals. Following this an Affymetrix gene array was performed in duplicate on a single sample and analysed using Genespring software.

The Affymetrix array showed that 900 genes were effected by BiP with >75% being down-regulated. The results of all three arrays showed that IL-1beta was reduced while IL-1 receptor antagonist was increased. HLA-DR, CD40 and CD86 were all downregulated as were c-fos, IKKalpha, and adhesion molecules CD54, alphav beta3, CD18 and CD11c. The chemokines GRO alpha, beta, and gamma were enhanced as were IL-6, MCP-1 and RANTES although several chemokine receptors were concomitantly downregulated (CCR1, CCR2 and CXCR4).

Changes in gene activation, following stimulation of human monocytes by BiP, effect antigen presentation, cell migration and the production of inflammatory cytokines.

Example 2

Confirmation and Optimisation of the Inhibition of the In Vitro Model of Cytokine Driven Osteoclastogenesis by BiP in Human and Mouse Systems

All in vitro experiments are carried out using human and mouse cells. The human cells are isolated from peripheral blood by density centrifugation (27) to isolate mononuclear cells. The mouse cells are isolated from femurs and tibiae of 5- to 8-wk-old adult mice as described previously (28). In both systems osteoclast differentiation is assessed by the number of cells counted positive for TRAP (mouse), or expression of vitronectin receptors (VnR) and/or F actin rings (human). Resorptive function in both systems is assessed by quantifying formation of resorption lacunae following culture of cells on dentine slices. Under the experimental conditions osteoclast cultures are harvested after 4-5 days (mouse) or 10-12 days (human), and resorption assays are performed after 7 and 14 days for mouse and human osteoclasts, respectively.

PBMC (human) or BMM (mouse) are prepared following overnight culture in M-CSF (25 ng/ml). To generate osteoclasts, M-CSF-dependent non-adherent cells are subsequently cultured with M-CSF (25 ng/ml) and RANKL (10 ng/ml) in the continuous presence and absence of BiP over a range of concentrations (0.02-20 μg/ml). Pulse studies, where BiP is added during the early stages of precursor differentiation, or after formation of multinucleated cells, is also carried out to determine the effects of BiP on the different stages of osteoclast differentiation. At the appropriate time, cultures are fixed and stained histochemically for TRAP activity (mouse), or stained for VnR and F-actin rings by immunolocalisation using the 23C6 antibody, and TRITC-phalloidin, respectively (human), and the number of osteoclasts is quantified. Resorption is quantified following removal of osteoclasts from dentine slices and staining with toluidine blue. Additional confirmation of the osteoclast differentiation data, particularly in mouse cells, is confirmed by molecular techniques using real-time PCR to measure the expression of osteoclast-specific marker genes—such as calcitonin receptor and cathepsin K.

Since BiP stimulates IL-10 production in PBMC(19), and IL-10 inhibits osteoclast differentiation (29) IL-10 production by the mouse and human osteoclast precursors is measured, following 24 h culture, at the protein level by ELISA or at the mRNA level by real-time PCR. Additional experiments, using neutralising anti-IL-10 or anti-IL-10 receptor monoclonal antibodies, will an assessment of whether any inhibitory effect observed with BiP is due to IL-10 alone or to other factors. The possibility of osteoclast numbers being reduced by apoptosis is also addressed, and cells treated with BiP are examined for apoptosis morphologically using DAPI staining, and biochemically using TUNEL assays.

Example 3

Interferes of BiP with the Major Cell Signalling Pathways Involved in Osteoclastogenesis and Bone Resorption This is investigated either directly, via inhibition of the phosphorylation and activation of molecules, from the cell surface through to transcription factors (e.g. RANK and c-Fms, TRAFs, c-Fos, NFATc1, MAPK [p38, jun and ER1/2], IKK and NF-κB, and Akt), or indirectly, by release of inhibitory cytokines, such as IL-10.

All in vitro experiments are carried out using human and mouse cells. The human cells are isolated from peripheral blood by density centrifugation (27) to isolate mononuclear cells. The mouse cells are isolated from femurs and tibiae of 5- to 8-wk-old adult mice as described previously (28). In both systems osteoclast differentiation is assessed by the number of cells counted positive for TRAP (mouse), or expression of vitronectin receptors (VnR) and/or F actin rings (human). Resorptive function in both systems is assessed by quantifying formation of resorption lacunae following culture of cells on dentine slices. Under the experimental conditions osteoclast cultures are harvested after 4-5 days (mouse) or 10-12 days (human), and resorption assays are performed after 7 and 14 days for mouse and human osteoclasts, respectively.

The expression of several pivotal proteins in the cell signalling cascade downstream from RANKL/RANK and M-CSF/c-Fms binding is studied. These include, for example, RANK and c-Fms, TRAF6, c-Fos and NFATc1, MAPK, IKK and NF-κB and Akt. These have been shown recently to be of paramount importance in osteoclastogenesis and therefore provide a starting point for analysing the mechanisms underlying the inhibitory effects of BiP. Without wishing to be bound by any particular theory, it is anticipated that BiP has the potential to exert its inhibitory effects on both osteoclast precursors as well as a mature osteoclasts. Thus, BMM and PBMC cultures are prepared in the presence of M-CSF and RANKL and BiP is added at a maximally effective concentration (as determined from Example 2) for a 24-72 h period either at the beginning of the culture, i.e. osteoclast precursors, or towards the end of the culture when multinucleated osteoclasts are clearly present. Cultures are harvested at the appropriate time and either RNA or protein extracts are prepared for quantitative real-time PCR and Western blotting analyses for expression of signalling molecules/transcription factors, including c-Fms, RANK, c-Fos, NFATc1, TRAF6, IKK and Akt. In some cases, phosphospecific antibodies against pERK1/2, pp 38, and pJNK are used to look at the effects on these MAPK family members following exposure to BiP for 5-60 min. Appropriate positive and negative controls are used for the real-time PCR and specific primers and fluorescent probes for all genes are designed and used. Protein lysates for Western blotting are prepared using the proteinase inhibitors as described before (30;31). The protein content is measured so equal loading of the polyacrylamide gel can be ensured and samples electrophoresed under denaturing conditions. The proteins are blotted onto nitrocellulose and probed with specific primary and secondary antibodies and visualised by enhanced chemiluminescence. All antibodies are available from Chemicon, Santa Cruz and Sigma.

These experiments can be used to determine which of the major signalling pathways that have been shown to play important roles in osteoclast differentiation and activation, are modulated by BiP. Moreover these studies will shed light on whether the mechanism of BiP action is different in regulating precursor cell differentiation versus activation of mature osteoclasts.

Example 4

Effectiveness of BiP Treatment In Vivo in Osteoclast Formation and Bone Resorption Using an Animal Model Designed to Promote Osteoclast Differentiation Oophorectomised CD1 mice spontaneously overproduce osteoclasts and develop an osteoporosis-like disease that will be treated with BiP at different stages of disease.

The mechanism of action of BiP in vivo is determined using models of human disease. In the study of bone loss in animal models of RA inflammatory cells, T lymphocytes and activated fibroblasts etc (9;10) which can express RANKL and induce bone resorption, and the production of cytokines—such as TNFα and IL-1β(32)—which drive osteoclastogenesis, can complicate experiments. Additionally, the T cell cytokine, IL-17 (7), can enhance this activity. Mouse material from the original BiP study of prevention and therapy of CIA is examined in detail for the presence of osteoclasts. Sections for TRAP are stained and the number of osteoclasts/section in each group assessed, or osteoclasts by in situ hybridisation of osteoclast marker genes—such as Cathepsin K or MMP-9 identified using routine techniques that are known to a person skilled in the art. This provides data for osteoclast development in an antigen-driven arthritis model where immune cells and cytokines play a role in a similar way to RA.

In an independent model of osteoclast activation and bone loss which is independent of an inflammatory response, a model that promotes bone destruction and osteoclast maturation—the oophorectomised mouse (33) is used. In the first instance, the protocol for BiP prevention of CIA is used in which a single dose of BiP prior to induction of disease prevented the symptoms measured one month post-induction (17) is used. Thus, in the oophorectomy (ovx) model, BiP is administered intravenously at three time points, to separate groups of 6 mice: either 1 week prior to ovx, at the time of ovx or post-ovx at weekly intervals to determine if BiP can prevent the induction of osteoclastic bone resorption following oestrogen withdrawal. Mice are sacrificed and bones examined at one-week intervals post-ovx up to 6 weeks. Parallel groups of control mice treated with vehicle or an irrelevant protein, such as human serum albumin, as well as sham controls are used. The bone mineral density and bone resorption is assessed and quantified by microCT and histological analysis and TRAP staining is used to elucidate the number of osteoclasts. These experiments are used to further investigate the role of BiP in preventing oophorectomy-induced bone loss.

Summary

BiP is a novel biological therapy for rheumatic diseases in which there is osteoclast activation. In vitro and in vivo experimental evidence is provided to support the assertion that that BiP inhibits osteoclastogenesis in human and murine in vitro osteoclastogenesis systems.

TABLE 1

Cytokine gene array data analysed by densitometry.

| | Upregulation | | | Downregulation | |
|---|---|---|---|---|---|
| | MO + BiP | MO | | MO + BiP | MO |
| L-1Ra | 26.7 ± 19.7 | 12.2 | ENA-78 | 4.2 ± 16.2 | 55 |
| L6 | 17 ± 18.2 | 6.7 | GROγ | 35.6 ± 25 | 47 |
| AMAC | 18.3 ± 5.3 | ND | IL-8 | 57.8 ± 20.4 | 80 |
| TNF RII | 4.1 ± 2.2 | ND | IL-1β | 189 | 204 |
| | | | LDGF | 5.4 ± 0.7 | 52 |
| | | | Integrin β1, β2, β4 | ND/ND/24 | 22/56/35 |
| | | | IFNγR1 | ND | 23 |

Peripheral blood monocytes were isolated and stimulated with either BiP (20 mg/ml) (MO+BiP) or left unstimulated (MO) for 24 h. The cytokine gene array autoradiographs were analysed by densitometry and normalised to give a percentage expression of maximum (100%) or gene activation was not detected (ND). The results shown are from two subjects for BiP stimulated monocytes and one subject for unstimulated monocytes. The results are shown as either upregulation or downregulation of BiP stimulated cytokine mRNA, in both samples, when compared with the control cells.

REFERENCES (1) Boyle W J, Simonet W S, Lacey D L. Osteoclast differentiation and activation. Nature 2003; 423(6937):337-342.
(2) Chambers T J. Regulation of the differentiation and function of osteoclasts. J Pathol 2000; 192(1):4-13.
(3) Roodman G D. Cell biology of the osteoclast. Exp Hematol 1999; 27(8):1229-1241.
(4) Suda T, Takahashi N, Udagawa N, Jimi E, Gillespie M T, Martin T J. Modulation of osteoclast differentiation and function by the new members of the tumor necrosis factor receptor and ligand families. Endocr Rev 1999; 20(3):345-357.
(5) Wagner E F, Karsenty G. Genetic control of skeletal development. Curr Opin Genet Dev 2001; 11(5):527-532.
(6) Degli-Esposti M. To die or not to die—the quest of the TRAIL receptors. J Leukoc Biol 1999; 65(5):535-542.
(7) Lubberts E, van den B L, Oppers-Walgreen B, Schwarzenberger P, Coenen-de Roo C J, Kolls J K et al. IL-17 promotes bone erosion in murine collagen-induced arthritis through loss of the receptor activator of NF-kappa B ligand/osteoprotegerin balance. J Immunol 2003; 170(5):2655-2662.
(8) Udagawa N. The mechanism of osteoclast differentiation from macrophages: possible roles of T lymphocytes in osteoclastogenesis. J Bone Miner Metab 2003; 21(6):337-343.
(9) Rifas L, Arackal S, Weitzmann M N. Inflammatory T cells rapidly induce differentiation of human bone marrow stromal cells into mature osteoblasts. J Cell Biochem 2003; 88(4):650-659.
(10) Takayanagi H, Iizuka H, Juji T, Nakagawa T, Yamamoto A, Miyazaki T et al. Involvement of receptor activator of nuclear factor kappaB ligand/osteoclast differentiation factor in osteoclastogenesis from synoviocytes in rheumatoid arthritis. Arthritis Rheum 2000; 43(2):259-269.
(11) Jimi E, Aoki K, Saito H, D'Acquisto F, May M J, Nakamura I et al. Selective inhibition of NF-kappaB blocks osteoclastogenesis and prevents inflammatory bone destruction in vivo. Nat Med 2004; 10(6):617-624.
(12) Eferl R, Wagner E F. AP-1: a double-edged sword in tumorigenesis. Nat Rev Cancer 2003; 3(11):859-868.
(13) Grigoriadis A E, Wang Z Q, Cecchini M G, Hofstetter W, Felix R, Fleisch H A et al. c-Fos: a key regulator of osteoclast-macrophage lineage determination and bone remodeling. Science 1994; 266(5184):443-448.
(14) Lee Z H, Kim H H. Signal transduction by receptor activator of nuclear factor kappa B in osteoclasts. Biochem Biophys Res Commun 2003; 305(2):211-214.
(15) Takayanagi H, Kim S, Koga T, Nishina H, Isshiki M, Yoshida H et al. Induction and activation of the transcription factor NFATc1 (NFAT2) integrate RANKL signaling in terminal differentiation of osteoclasts. Dev Cell 2002; 3(6):889-901.
(16) Walsh N C, Gravallese E M. Bone loss in inflammatory arthritis: mechanisms and treatment strategies. Curr Opin Rheumatol 2004; 16(4):419-427.
(17) Corrigall V M, Bodman-Smith M D, Fife M S, Canas B, Myers L K, Wooley P et al. The human endoplasmic reticulum molecular chaperone BiP is an autoantigen for rheumatoid arthritis and prevents the induction of experimental arthritis. J Immunol 2001; 166(3):1492-1498.
(18) Bodman-Smith M D, Corrigall V M, Kemeny D M, Panayi G S. BiP, a putative autoantigen in rheumatoid arthritis, stimulates IL-10-producing CD8-positive T cells from normal individuals. Rheumatology (Oxford) 2003; 42(5):637-644.
(19) Corrigall V M, Bodman-Smith M D, Brunst M, Cornell H, Panayi G S. The stress protein, BiP, stimulates human peripheral blood mononuclear cells to express an anti-inflammatory cytokine profile and to inhibit antigen presenting cell function: relevance to the treatment of inflammatory arthritis. Arthritis Rheum 2004; 50:1167-1171.
(20) Miossec P, Chomarat P, Dechanet J, Moreau J F, Roux J P, Delmas P et al. Interleukin-4 inhibits bone resorption through an effect on osteoclasts and proinflammatory cytokines in an ex vivo model of bone resorption in rheumatoid arthritis. Arthritis Rheum 1994; 37(12):1715-1722.
(21) Yang S Y, Wu B, Mayton L, Mukherjee P, Robbins P D, Evans C H et al. Protective effects of IL-1Ra or vIL-10 gene transfer on a murine model of wear debris-induced osteolysis. Gene Ther 2004; 11(5):483-491.
(22) Vittecoq O, Corrigall V M, Bodman-Smith M D, Panayi G S. The molecular chaperone BiP (GRP78) inhibits the differentiation of normal human monocytes into immature dendritic cells. Rheumatology (Oxford) 2003; 42 suppl:43.
(23) Nair S P, Meghji S, Reddi K, Poole S, Miller A D, Henderson B. Molecular chaperones stimulate bone resorption. Calcif Tissue Int 1999; 64(3):214-218.
(24) Teti A, Migliaccio S, Baron R. The role of the alphaV-beta3 integrin in the development of osteolytic bone metastases: a pharmacological target for alternative therapy? Calcif Tissue Int 2002; 71(4):293-299.
(25) Vignery A. Osteoclasts and giant cells: macrophage-macrophage fusion mechanism. Int J Exp Pathol 2000; 81(5):291-304.
(26) Sodek J, Zhu B, Huynh M H, Brown T J, Ringuette M. Novel functions of the matricellular proteins osteopontin and osteonectin/SPARC. Connect Tissue Res 2002; 43(2-3):308-319.
(27) Corrigall V M, Solau-Gervais E, Panayi G S. Lack of CD80 expression by fibroblast-like synoviocytes leading to anergy in T lymphocytes. Arthritis Rheum 2000; 43(7):1606-1615.
(28) Li X, Udagawa N, Takami M, Sato N, Kobayashi Y, Takahashi N. p38 Mitogen-activated protein kinase is crucially involved in osteoclast differentiation but not in cytokine production, phagocytosis, or dendritic cell differentiation of bone marrow macrophages. Endocrinology 2003; 144(11):4999-5005.
(29) Hong M H, Williams H, Jin C H, Pike J W. The inhibitory effect of interleukin-10 on mouse osteoclast formation involves novel tyrosine-phosphorylated proteins. J Bone Miner Res 2000; 15(5):911-918.
(30) Corrigall V M, Arastu M, Khan S, Shah C, Fife M, Smeets T et al. Functional IL-2 receptor beta (CD122) and gamma (CD132) chains are expressed by fibroblast-like synoviocytes: activation by IL-2 stimulates monocyte chemoattractant protein-1 production. J Immunol 2001; 166(6):4141-4147.
(31) Sunters A, Thomas D P, Yeudall W A, Grigoriadis A E. Accelerated cell cycle progression in osteoblasts overexpressing the c-fos proto-oncogene: induction of cyclin A and enhanced CDK2 activity. J Biol Chem 2004; 279(11): 9882-9891.
(32) Zwerina J, Hayer S, Tohidast-Akrad M, Bergmeister H, Redlich K, Feige U et al. Single and combined inhibition of tumor necrosis factor, interleukin-1, and RANKL pathways in tumor necrosis factor-induced arthritis: effects on synovial inflammation, bone erosion, and cartilage destruction. Arthritis Rheum 2004; 50(1):277-290.
(33) Libouban H, Moreau M F, Basle M F, Bataille R, Chappard D. Increased bone remodeling due to ovariectomy dramatically increases tumoral growth in the 5T2 multiple myeloma mouse model. Bone 2003; 33(3):283-292.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in biochemistry and molecular biology or related fields are intended to be within the scope of the following claims.

The invention claimed is:

1. A method for treating bone loss or bone resorption in a mammal comprising administering to said mammal binding immunoglobulin protein (BiP) having the amino sequence set forth in SEQ ID NO. 1 or SEQ ID NO. 2 or a fragment of the amino acid sequence of SEQ ID NO: 1 or SEQ ID NO: 2 that comprises the biological activity of inhibiting bone resorption to cause a beneficial preventative or therapeutic effect.

2. The method of claim 1, wherein the bone loss or bone resorption is associated with muscoskeletal disease.

3. The method of claim 2, wherein the muscoskeletal disease is osteoporosis.

4. A method for treating bone resorption in a mammal comprising administering to said mammal binding immunoglobulin protein (BiP) having the amino acid sequence set forth in SEQ ID NO. 1 or SEQ ID NO. 2 or a fragment of the amino acid sequence of SEQ ID NO: 1 or SEQ ID NO: 2 that comprises the biological activity of inhibiting bone resorption to cause a beneficial preventative or therapeutic effect.

5. A method for inhibiting osteoclast development comprising contacting an osteoclast with binding immunoglobulin protein (BiP) having the amino acid sequence set forth in SEQ ID NO. 1 or SEQ ID NO. 2 or a fragment of the amino acid sequence of SEQ ID NO: 1 or SEQ ID NO: 2 that comprises the biological activity of inhibiting bone resorption.

6. The method of claim 5, wherein the osteoclast is an osteoclast precursor, a multi-nucleated precursor or a mature osteoclast.

7. The method according to claim 5, wherein the inhibiting osteoclast development comprises inhibiting, reducing or preventing osteoclast development or maturation.

8. The method according to claim 5, wherein the method is performed in vivo or in vitro.

9. A method for the treatment of osteoporosis in an animal comprising administering to said animal a composition comprising binding immunoglobulin protein (BiP) having the amino acid sequence set forth in SEQ ID NO. 1 or SEQ ID NO. 2 or a fragment of the amino acid sequence of SEQ ID NO: 1 or SEQ ID NO: 2 that comprises the biological activity of inhibiting bone resorption in an amount effective to alleviate one or more symptoms of osteoporosis.

* * * * *

SEQUENCE LISTING

```
<160> NUMBER OF SEQ ID NOS: 3

<210> SEQ ID NO 1
<211> LENGTH: 639
<212> TYPE: PRT
<213> ORGANISM: Homo sapiens

<400> SEQUENCE: 1

Met Glu Glu Asp Lys Lys Glu Asp Val Gly Thr Val Val Gly Ile Asp
1               5                   10                  15

Leu Gly Thr Thr Tyr Ser Cys Val Gly Val Phe Lys Asn Gly Arg Val
            20                  25                  30

Glu Ile Ile Ala Asn Asp Gln Gly Asn Arg Ile Thr Pro Ser Tyr Val
        35                  40                  45

Ala Phe Thr Pro Glu Gly Glu Arg Leu Ile Gly Asp Ala Ala Lys Asn
    50                  55                  60

Gln Leu Thr Ser Asn Pro Glu Asn Thr Val Phe Asp Ala Lys Arg Leu
65                  70                  75                  80

Ile Gly Arg Thr Trp Asn Asp Pro Ser Val Gln Gln Asp Ile Lys Phe
                85                  90                  95

Leu Pro Phe Lys Val Val Glu Lys Lys Thr Lys Pro Tyr Ile Gln Val
            100                 105                 110

Asp Ile Gly Gly Gly Gln Thr Lys Thr Phe Ala Pro Glu Glu Ile Ser
        115                 120                 125

Ala Met Val Leu Thr Lys Met Lys Glu Thr Ala Glu Ala Tyr Leu Gly
    130                 135                 140

Lys Lys Val Thr His Ala Val Val Thr Val Pro Ala Tyr Phe Asn Asp
145                 150                 155                 160

Ala Gln Arg Gln Ala Thr Lys Asp Ala Gly Thr Ile Ala Gly Leu Asn
                165                 170                 175

Val Met Arg Ile Ile Asn Glu Pro Thr Ala Ala Ala Ile Ala Tyr Gly
            180                 185                 190

Leu Asp Lys Arg Glu Gly Glu Lys Asn Ile Leu Val Phe Asp Leu Gly
        195                 200                 205

Gly Gly Thr Phe Asp Val Ser Leu Leu Thr Ile Asp Asn Gly Val Phe
    210                 215                 220
```

-continued

```
Glu Val Ala Thr Asn Gly Asp Thr His Leu Gly Gly Glu Asp Phe
225                 230                 235                 240

Asp Gln Arg Val Met Glu His Phe Ile Lys Leu Tyr Lys Lys Thr
            245                 250                 255

Gly Lys Asp Val Arg Lys Asp Asn Arg Ala Val Gln Lys Leu Arg Arg
                260                 265                 270

Glu Val Glu Lys Ala Lys Arg Ala Leu Ser Ser Gln His Gln Ala Arg
        275                 280                 285

Ile Glu Ile Glu Ser Phe Tyr Glu Gly Glu Asp Phe Ser Glu Thr Leu
    290                 295                 300

Thr Arg Ala Lys Phe Glu Glu Leu Asn Met Asp Leu Phe Arg Ser Thr
305                 310                 315                 320

Met Lys Pro Val Gln Lys Val Leu Glu Asp Ser Asp Leu Lys Lys Ser
                325                 330                 335

Asp Ile Asp Glu Ile Val Leu Val Gly Gly Ser Thr Arg Ile Pro Lys
                340                 345                 350

Ile Gln Gln Leu Val Lys Glu Phe Phe Asn Gly Lys Glu Pro Ser Arg
            355                 360                 365

Gly Ile Asn Pro Asp Glu Ala Val Ala Tyr Gly Ala Ala Val Gln Ala
        370                 375                 380

Gly Val Leu Ser Gly Asp Gln Asp Thr Gly Asp Leu Val Leu Leu Asp
385                 390                 395                 400

Val Cys Pro Leu Thr Leu Gly Ile Glu Thr Val Gly Gly Val Met Thr
                405                 410                 415

Lys Leu Ile Pro Arg Asn Thr Val Val Pro Thr Lys Lys Ser Gln Ile
                420                 425                 430

Phe Ser Thr Ala Ser Asp Asn Gln Pro Thr Val Thr Ile Lys Val Tyr
            435                 440                 445

Glu Gly Glu Arg Pro Leu Thr Lys Asp Asn His Leu Leu Gly Thr Phe
        450                 455                 460

Asp Leu Thr Gly Ile Pro Pro Ala Pro Arg Gly Val Pro Gln Ile Glu
465                 470                 475                 480

Val Thr Phe Glu Ile Asp Val Asn Gly Ile Leu Arg Val Thr Ala Glu
                485                 490                 495

Asp Lys Gly Thr Gly Asn Lys Asn Lys Ile Thr Ile Thr Asn Asp Gln
                500                 505                 510

Asn Arg Leu Thr Pro Glu Glu Ile Glu Arg Met Val Asn Asp Ala Glu
            515                 520                 525

Lys Phe Ala Glu Glu Asp Lys Lys Leu Lys Glu Arg Ile Asp Thr Arg
        530                 535                 540

Asn Glu Leu Glu Ser Tyr Ala Tyr Ser Leu Lys Asn Gln Ile Gly Asp
545                 550                 555                 560

Lys Glu Lys Leu Gly Gly Lys Leu Ser Ser Glu Asp Lys Glu Thr Met
                565                 570                 575

Glu Lys Ala Val Glu Glu Lys Ile Glu Trp Leu Glu Ser His Gln Asp
            580                 585                 590

Ala Asp Ile Glu Asp Phe Lys Ala Lys Lys Glu Leu Glu Glu Ile
        595                 600                 605

Val Gln Pro Ile Ile Ser Lys Leu Tyr Gly Ser Ala Gly Pro Pro
        610                 615                 620

Thr Gly Glu Glu Asp Thr Ala Glu Leu His His His His His His
625                 630                 635
```

<210> SEQ ID NO 2
<211> LENGTH: 633
<212> TYPE: PRT
<213> ORGANISM: Homo sapiens

<400> SEQUENCE: 2

Met Glu Glu Asp Lys Lys Glu Asp Val Gly Thr Val Val Gly Ile Asp
1               5                   10                  15

Leu Gly Thr Thr Tyr Ser Cys Val Gly Val Phe Lys Asn Gly Arg Val
            20                  25                  30

Glu Ile Ile Ala Asn Asp Gln Gly Asn Arg Ile Thr Pro Ser Tyr Val
        35                  40                  45

Ala Phe Thr Pro Glu Gly Glu Arg Leu Ile Gly Asp Ala Ala Lys Asn
    50                  55                  60

Gln Leu Thr Ser Asn Pro Glu Asn Thr Val Phe Asp Ala Lys Arg Leu
65                  70                  75                  80

Ile Gly Arg Thr Trp Asn Asp Pro Ser Val Gln Gln Asp Ile Lys Phe
                85                  90                  95

Leu Pro Phe Lys Val Val Glu Lys Lys Thr Lys Pro Tyr Ile Gln Val
            100                 105                 110

Asp Ile Gly Gly Gly Gln Thr Lys Thr Phe Ala Pro Glu Glu Ile Ser
        115                 120                 125

Ala Met Val Leu Thr Lys Met Lys Glu Thr Ala Glu Ala Tyr Leu Gly
    130                 135                 140

Lys Lys Val Thr His Ala Val Val Thr Val Pro Ala Tyr Phe Asn Asp
145                 150                 155                 160

Ala Gln Arg Gln Ala Thr Lys Asp Ala Gly Thr Ile Ala Gly Leu Asn
                165                 170                 175

Val Met Arg Ile Ile Asn Glu Pro Thr Ala Ala Ala Ile Ala Tyr Gly
            180                 185                 190

Leu Asp Lys Arg Glu Gly Glu Lys Asn Ile Leu Val Phe Asp Leu Gly
        195                 200                 205

Gly Gly Thr Phe Asp Val Ser Leu Leu Thr Ile Asp Asn Gly Val Phe
    210                 215                 220

Glu Val Val Ala Thr Asn Gly Asp Thr His Leu Gly Gly Glu Asp Phe
225                 230                 235                 240

Asp Gln Arg Val Met Glu His Phe Ile Lys Leu Tyr Lys Lys Lys Thr
                245                 250                 255

Gly Lys Asp Val Arg Lys Asp Asn Arg Ala Val Gln Lys Leu Arg Arg
            260                 265                 270

Glu Val Glu Lys Ala Lys Arg Ala Leu Ser Ser Gln His Gln Ala Arg
        275                 280                 285

Ile Glu Ile Glu Ser Phe Tyr Glu Gly Glu Asp Phe Ser Glu Thr Leu
    290                 295                 300

Thr Arg Ala Lys Phe Glu Glu Leu Asn Met Asp Leu Phe Arg Ser Thr
305                 310                 315                 320

Met Lys Pro Val Gln Lys Val Leu Glu Asp Ser Asp Leu Lys Lys Ser
                325                 330                 335

Asp Ile Asp Glu Ile Val Leu Val Gly Gly Ser Thr Arg Ile Pro Lys
            340                 345                 350

Ile Gln Gln Leu Val Lys Glu Phe Phe Asn Gly Lys Glu Pro Ser Arg
        355                 360                 365

Gly Ile Asn Pro Asp Glu Ala Val Ala Tyr Gly Ala Ala Val Gln Ala
    370                 375                 380

Gly Val Leu Ser Gly Asp Gln Asp Thr Gly Asp Leu Val Leu Leu Asp

```
                        385                 390                 395                 400

Val Cys Pro Leu Thr Leu Gly Ile Glu Thr Val Gly Gly Val Met Thr
                    405                 410                 415

Lys Leu Ile Pro Arg Asn Thr Val Pro Thr Lys Lys Ser Gln Ile
                420                 425                 430

Phe Ser Thr Ala Ser Asp Asn Gln Pro Thr Val Thr Ile Lys Val Tyr
                435                 440                 445

Glu Gly Glu Arg Pro Leu Thr Lys Asp Asn His Leu Leu Gly Thr Phe
            450                 455                 460

Asp Leu Thr Gly Ile Pro Pro Ala Pro Arg Gly Val Pro Gln Ile Glu
465                 470                 475                 480

Val Thr Phe Glu Ile Asp Val Asn Gly Ile Leu Arg Val Thr Ala Glu
                485                 490                 495

Asp Lys Gly Thr Gly Asn Lys Asn Lys Ile Thr Ile Thr Asn Asp Gln
                500                 505                 510

Asn Arg Leu Thr Pro Glu Glu Ile Glu Arg Met Val Asn Asp Ala Glu
            515                 520                 525

Lys Phe Ala Glu Glu Asp Lys Lys Leu Lys Glu Arg Ile Asp Thr Arg
        530                 535                 540

Asn Glu Leu Glu Ser Tyr Ala Tyr Ser Leu Lys Asn Gln Ile Gly Asp
545                 550                 555                 560

Lys Glu Lys Leu Gly Gly Lys Leu Ser Ser Asp Lys Glu Thr Met
                565                 570                 575

Glu Lys Ala Val Glu Glu Lys Ile Glu Trp Leu Glu Ser His Gln Asp
            580                 585                 590

Ala Asp Ile Glu Asp Phe Lys Ala Lys Lys Lys Glu Leu Glu Glu Ile
        595                 600                 605

Val Gln Pro Ile Ile Ser Lys Leu Tyr Gly Ser Ala Gly Pro Pro Pro
    610                 615                 620

Thr Gly Glu Glu Asp Thr Ala Glu Leu
625                 630

<210> SEQ ID NO 3
<211> LENGTH: 1917
<212> TYPE: DNA
<213> ORGANISM: Homo sapiens

<400> SEQUENCE: 3
atggaggagg acaagaagga ggacgtgggc acggtggtcg gcatcgacct ggggaccacc     60
tactcctgcg tcggcgtgtt caagaacggc cgcgtggaga tcatcgccaa cgatcagggc    120
aaccgcatca cgccgtccta tgtcgccttc actcctgaag ggaacgtcct gattggcgat    180
gccgccaaga accagctcac ctccaacccc gagaacacgg tctttgacgc caagcggctc    240
atcggccgca cgtggaatga cccgtctgtg cagcaggaca tcaagttctt gccgttcaag    300
gtggttgaaa agaaaactaa accatacatt caagttgata ttggaggtgg cacaacaaag    360
acatttgctc ctgaagaaat ttctgccatg gttctcacta aaatgaaaga aaccgctgag    420
gcttatttgg gaagaaggt tacccatgca gttgttactg taccagccta tttaatgat    480 gcccaacgcc aagcaaccaa agacgctgga actattgctg cctaaatgt tatgaggatc    540 atcaacgagc ctacggcagc tgctattgct tatggcctgg ataagaggga ggggagaag    600 aacatcctgg tgtttgacct gggtggcgga accttcgatg tgtctcttct caccattgac    660
aatggtgtct tcgaagttgt ggccactaat ggagatactc atctgggtgg agaagacttt    720
gaccagcgtg tcatggaaca cttcatcaaa ctgtacaaaa agaagacggg caaagatgtc    780
```

```
                                                        -continued
aggaaagaca atagagctgt gcagaaactc cggcgcgagg tagaaaaggc caaacgggcc      840
ctgtcttctc agcatcaagc aagaattgaa attgagtcct tctatgaagg agaagacttt      900
tctgagaccc tgactcgggc caaatttgaa gagctcaaca tggatctgtt ccggtctact      960
atgaagcccg tccagaaagt gttggaagat tctgatttga agaagtctga tattgatgaa     1020
attgttcttg ttggtggctc gactcgaatt ccaaagattc agcaactggt taaagagttc     1080
ttcaatggca aggaaccatc ccgtggcata aacccagatg aagctgtagc gtatggtgct     1140
gctgtccagg ctggtgtgct ctctggtgat caagatacag gtgacctggt actgcttgat     1200
gtatgtcccc ttacacttgg tattgaaact gtgggaggtg tcatgaccaa actgattcca     1260
aggaacacag tggtgcctac caagaagtct cagatctttt ctacagcttc tgataatcaa     1320
ccaactgtta caatcaaggt ctatgaaggt gaaagacccc tgacaaaaga caatcatctt     1380
ctgggtacat ttgatctgac tggaattcct cctgctcctc gtggggtccc acagattgaa     1440
gtcacctttg agatagatgt gaatggtatt cttcgagtga cagctgaaga caagggtaca     1500
gggaacaaaa ataagatcac aatcaccaat gaccagaatc gcctgacacc tgaagaaatc     1560
gaaaggatgg ttaatgatgc tgagaagttt gctgaggaag acaaaaagct caaggagcgc     1620
attgatacta gaaatgagtt ggaaagctat gcctattctc taaagaatca gattggagat     1680
aaagaaaagc tgggaggtaa actttcctct gaagataagg agaccatgga aaaagctgta     1740
gaagaaaaga ttgaatggct ggaaagccac caagatgctg acattgaaga cttcaaagct     1800
aagaagaagg aactggaaga aattgttcaa ccaattatca gcaaactcta tggaagtgca     1860
ggccctcccc caactggtga agaggataca gcagaactcc accaccacca ccaccac      1917
```